United States Patent
Maisenhoelder et al.

(10) Patent No.: US 7,215,850 B2
(45) Date of Patent: May 8, 2007

(54) WAVEGUIDE PLATE AND PROCESS FOR ITS PRODUCTION AND MICROTITRE PLATE

(75) Inventors: Bernd Maisenhoelder, Zürich (CH); Johannes Edlinger, Frastanz (AT); Claus Heine, Maienfeld (CH); Michael Pawlak, Laufenburg (DE); Gert Duveneck, Bad Krozingen (DE)

(73) Assignees: OC Oerlikon Balzers AG, Balzers (LI); Zeptosens AG, Witterswil (CH)

( * ) Notice: Subject to any disclaimer, the term of this patent is extended or adjusted under 35 U.S.C. 154(b) by 27 days.

(21) Appl. No.: 11/208,765

(22) Filed: Aug. 23, 2005

(65) Prior Publication Data

US 2006/0008206 A1    Jan. 12, 2006

Related U.S. Application Data

(60) Division of application No. 09/916,114, filed on Jul. 27, 2001, now Pat. No. 6,961,490, which is a continuation-in-part of application No. 09/497,129, filed on Feb. 3, 2000, now Pat. No. 6,510,263.

(30) Foreign Application Priority Data

Jan. 27, 2000   (CH) .............................. 2000/160/00

(51) Int. Cl.
    *G02B 6/34*     (2006.01)
(52) U.S. Cl. ............................................. 385/37; 430/5
(58) Field of Classification Search ............... None
See application file for complete search history.

(56) References Cited

U.S. PATENT DOCUMENTS 4,729,640 A * 3/1988 Sakata .................. 349/201
4,806,454 A    2/1989 Yoshida
5,004,673 A    4/1991 Vlannes
5,082,629 A * 1/1992 Burgess et al. .......... 422/82.11
5,225,039 A    7/1993 Ohguri (Continued)

FOREIGN PATENT DOCUMENTS

DE    4410258    10/1994
EP    0566886    10/1993

OTHER PUBLICATIONS

European Search Report dated Oct. 14, 2005 with an English translation of the pertinent portion (three (3) pages).

*Primary Examiner*—Rodney Bovernick
*Assistant Examiner*—Mike Stahl
(74) *Attorney, Agent, or Firm*—Crowell & Moring LLP

(57) ABSTRACT

A waveguide plate and a process for making the waveguide plate with a plate-like glass substrate (1), carrying a waveguiding layer (2), with at least one coupling grating on the surface carrying said waveguiding layer (2), which coupling grating is formed as a grating of lines with a period between 150 nm and 1000 nm, the extension of said grating being at least 5 cm with lines parallel to one another, wherein the coupling angle ($\theta$) varies by not more than 0.1°/cm along a line of said grating and wherein the absolute value of the deviation of the coupling angle ($\theta$) on said waveguide plate, from a predefined desired value, does not exceed 0.5°. The deviation from the average value of the coupling angle does not exceed 0.3°, preferably not 0.15° on the whole waveguide plate. The waveguide plate is suitable as part of a sensor platform and of an arrangement of sample compartments for chemo-and bioanalytical investigations in order to produce a coupling grating formed as a line grating with a grating period between 100 nm and 2500 nm.

12 Claims, 9 Drawing Sheets

U.S. PATENT DOCUMENTS

| | | | | |
|---|---|---|---|---|
| 5,320,918 A | * | 6/1994 | Raab et al. | 430/4 |
| 5,413,884 A | * | 5/1995 | Koch et al. | 430/5 |
| 5,480,687 A | | 1/1996 | Heming et al. | |
| 5,501,925 A | * | 3/1996 | Smith et al. | 430/5 |
| 5,652,818 A | | 7/1997 | Byron | |
| 5,715,039 A | * | 2/1998 | Fukuda et al. | 355/53 |
| 5,718,738 A | * | 2/1998 | Kohnke et al. | 65/31 |
| 5,738,825 A | * | 4/1998 | Rudigier et al. | 422/82.11 |
| 5,759,744 A | | 6/1998 | Brueck | |
| 5,760,960 A | | 6/1998 | Lin et al. | |
| 5,786,116 A | * | 7/1998 | Rolfson | 430/5 |
| 5,965,890 A | * | 10/1999 | Hanson | 250/350 |
| 5,982,963 A | | 11/1999 | Feng | |
| 6,013,396 A | * | 1/2000 | Capodieci | 430/5 |
| 6,218,194 B1 | * | 4/2001 | Lyndin et al. | 436/518 |
| 6,744,949 B2 | * | 6/2004 | Takeuchi et al. | 385/37 |
| 6,751,381 B1 | * | 6/2004 | Popelek et al. | 385/37 |
| 2002/0180941 A1 | * | 12/2002 | Hansen | 355/53 |
| 2003/0091284 A1 | * | 5/2003 | Maisenholder et al. | 385/37 |
| 2003/0112515 A1 | * | 6/2003 | Nakabayashi | 359/571 |

\* cited by examiner

WAVEGUIDE PLATE AND PROCESS FOR ITS PRODUCTION AND MICROTITRE PLATE

CROSS-REFERENCE TO RELATED APPLICATIONS

This application is a continuation-in-part of U.S. application Ser. No. 09/497,129 filed on Feb. 3, 2000, now U.S. Pat. No. 6,510,263.

BACKGROUND OF THE INVENTION

The invention relates to a waveguide plate and a process for its production and a microtitre plate comprising such a waveguide plate and as used, for example, for analytical purposes in the biochemical and medical sector, as well as a sensor platform based on a waveguide plate, an evanescent field sensor plate, according to the invention as well as arrangements of sample compartments, with a waveguide plate or a sensor platform according to the invention as a boundary surface of said arrangement of sample compartments. The invention also relates to an optical coupler and a device for monitoring such a coupler.

The process according to the invention is suitable for producing optical elements with grating structures. Evanescent field sensor plates and microtitre plates produced according to the process can be used in chemical and biomolecular analyses. Optical couplers have applications in communications technology, and more particularly in data transmission via fibre networks. A potential application of a particular coupler according to the invention is in a device for monitoring the wavelength of laser light in a fiber network.

EP-A-0 602 829 discloses a process for producing a grating structure on a substrate, for example for a DBR semiconductor laser, in which first a phase mask is produced and then the substrate, e.g. InP, is exposed at the Lithrow angle, through the phase mask. The exposure can be effected by means of an Hg-Xe arc lamp having a light source diameter of 0.25 mm, three lines around 365 nm wavelength being filtered out. The substrate is located close to the phase mask, i.e. at a distance of not more than 10 microns.

To produce the phase mask, a quartz substrate is covered with three layers, a photoresist layer, a thin germanium layer and finally a layer of a resist sensitive to electron beams. The uppermost layer is then structured by inscribing by means of electron beams, developing the uppermost layer and removing the unexposed parts. The structure is transferred to the layers underneath by reactive ion etching, initially with $CF_3Br$ and then with $O_2$, and finally to the quartz substrate itself by a further step of reactive ion etching, whereupon the residues of the layers are removed. The grating constant may be, for example, between 190 nm and 250 nm. The phase mask may be several centimeters long and the grating may extend over its entire length. However, the length of the lines is, as a rule, only 5–20 microns. Greater lengths are possible but require very long processing times. In practice, gratings of more than 1 $mm^2$ can hardly be produced with reasonable effort and good accuracy. In particular, stitching errors during inscribing by means of electron beams cannot be avoided.

From U.S. Pat. No. 5,675,691 a plate is known on which coupling gratings are produced by applying a layer of TiO2, Ta2O5, HfO2, Y2O3, Al2O3, Nb2O5, nitride or oxynitride of Al, Si or Hf to a substrate of glass, in particular quartz glass, ceramic, or predominantly organic material. It is being possible to provide a 20 nm thick intermediate layer, e.g. of SiO2, and to structure it by ablation or modification of the refractive index by means of exposure to two superimposed beams of an excimer laser or to a beam modified by a mask. Instead, it is also possible to structure an intermediate layer, e.g. of TiO2, in which the ablation barrier is lower and which is applied either to the layer or directly to the substrate and, in the latter case, is superimposed by the layer after structuring. The grating periods are, for example, 375 nm or 440 nm. The grating surface area is freely selectable and may be, for example, 1 mm×1 mm or 8 mm×8 mm.

From U.S. Pat. No. 5,822,472 an evanescent field sensor plate for chemical analyses is known which bears a 40 nm to 160 nm thick layer of TiO2, ZnO, Nb2O5, Ta2O5, HfO2 or ZrO2 on a support of plastic, glass or quartz. An intermediate layer of nonluminescent material with a low refractive index, e.g., quartz having a thickness of 100 nm, for example, which at the same time serves as an adhesion promoter, may be arranged in between. An input coupling grating and an output coupling grating are provided which are created by known photolithographic or holographic and etching methods, either in the support or in the layer, and have a grating period of between 200 nm and 1000 nm. The gratings may have dimensions of 2 mm (parallel to the lines)×4 mm, with a total surface area of the wave-guide plate of 12 mm×20 mm.

From J. Duebendorfer and R. E. Kunz: "Compact integrated optical immunosensor using replicated chirped coupling grating sensor chips", Applied Optics, 37/10 (1 Apr. 1998), a further evanescent field sensor plate comprising a polycarbonate support plate is known into which a modulated input coupling grating having a grating period varying between 420 nm and 422.8 nm and an output coupling grating having a grating period varying between 595.1 nm and 600.8 nm were embossed. Thereafter, a TiO2 layer having a thickness of 137 nm and a refractive index of 2.346 was applied by means of low-temperature DC magnetron sputtering, and finally the evanescent field sensor plate was silanised. The input coupling angle is about −9.5_ and the output coupling angle is about 22.5_.

From U.S. Pat. No. 5,738,825 a microtitre plate can be obtained which has a 20 nm to 1000 nm, preferably 30 nm to 500 nm thick layer of $TiO_2$, $Ta_2O_5$, $HfO_2$, $ZrO_2$, $SiO_2$, $Si_3N_4$, $Al_2O_3$, $Nb_2O_5$ nitride or oxynitride of Al, Si or Hf applied to its bottom surface, this layer being covered by a plastic layer. Input and output coupling gratings are mounted underneath each cavity. The gratings have a grating period between 330 nm and 1000 nm, in particular about 400 nm to 800 nm, and are produced by lithographic or mechanical methods.

From CH-A-688 165 a wave-guide plate comprising a substrate of plastic, e.g. polycarbonate, is known whose surface was structured mechanically—by deep drawing, embossing or during its injection moulding—and in particular provided with a coupling grating, and bears a layer of $TiO_2$, $Ta_2O_5$, $ZrO_2$, $Al_2O_3$, $SiO_2$—$TiO_2$, $HfO_2$, $Y_2O_3$, $Nb_2O_5$, silicon nitride, oxynitride, $SiO_xN_y$, $HfO_xN_y$, $AlO_xN_y$, $TiO_xN_y$, $MgF_2$ or $CaF_2$ applied by a PVD method. To reduce the attenuation losses, an approximately 20 nm thick intermediate layer applied to the substrate prior to the layer and comprising an inorganic dielectric material such as SiO2 is provided which at the same time serves as an adhesion promoter.

All plates described above are produced by processes with which no satisfactory uniformity of the coupling grating can be achieved, so that the coupling angle varies relatively widely. Consequently, the relative angular position of the exposure unit and plate must be optimised laboriously in each step when the plate is to be used as a waveguide or an evanescent field sensor plate. The filter characteristics are unsatisfactory and not sufficient, for instance, for selectively filtering a particular wavelength from a group of very closely spaced wavelengths, when the plate is used as an optical coupler in communications technology. Some of the processes described are also very laborious or do not allow very large numbers of pieces of constant quality to be made.

SUMMARY OF THE INVENTION

It is the object of the invention to provide a waveguide plate which permits feasible rapid analysis with little effort. In addition, it is intended to provide a microtitre plate based on such a waveguide plate. As a result of the limits which are narrow also with large grating lengths and within which the coupling angle varies, it is possible simultaneously to expose and to read out larger parts of the waveguide plate or microtitre plate. Successive exposures of different parts of the waveguide plate or microtitre plate are also simplified since reoptimization of the relative angle between it and the exposure unit is not required or in any case very easy.

Furthermore, it is the object of the invention to provide a process for producing a waveguide plate according to the invention, which permits the creation of large gratings in particular having long parallel lines with great precision, provides freedom of design with regard to the arrangement of the gratings and is simple and economical. The process according to the invention furthermore permits the production of large series of waveguide plates of constant quality and having optical properties, such as coupling efficiencies and in particular coupling angles, which are within narrow limits. The process according to the invention also permits the production of large series of optical elements of constant quality and with optical properties such as coupling efficiencies and, in particular, coupling angles which are constant within narrow limits.

The process according to the invention furthermore permits the production of large series of optical elements of constant quality and with optical properties such as coupling efficiencies and, in particular, coupling angles which are constant within narrow limits.

It is also an object of the invention to provide a sensor platform and an arrangement of sample compartments, based on a waveguide plate according to the invention Additionally, a highly precise optical element is to be provided such as can be produced by the process according to the invention. In particular, the optical element can be formed as a waveguide plate or an evanescent field sensor plate or as a microtitre plate based on such a plate. In view of the narrow limits within which, even in long gratings, the coupling angle varies, it is possible to simultaneously illuminate and read out larger parts of the waveguide plate or evanescent field sensor plate or microtitre plate. Successive exposure of different parts of the waveguide plate or the evanescent field sensor plate or microtitre plate is also simplified since reoptimization of the relative angular position of this plate and the exposing unit is not required or in any case greatly simplified.

The optical element can also be formed as an optical coupler for communications technology. In this case, the high precision present even in large grating structures guarantees excellent filter characteristics, and particularly a very-narrow-band selection of individual wavelengths, so that, for instance, a wavelength multiplexing involving very closely spaced wavelengths is possible, which raises the transmission capacity.

Other objects, advantages and novel features of the present invention will become apparent from the following detailed description of the invention when considered in conjunction with the accompanying drawings.

DESCRIPTION OF THE PREFERRED EMBODIMENTS

Figure 1:
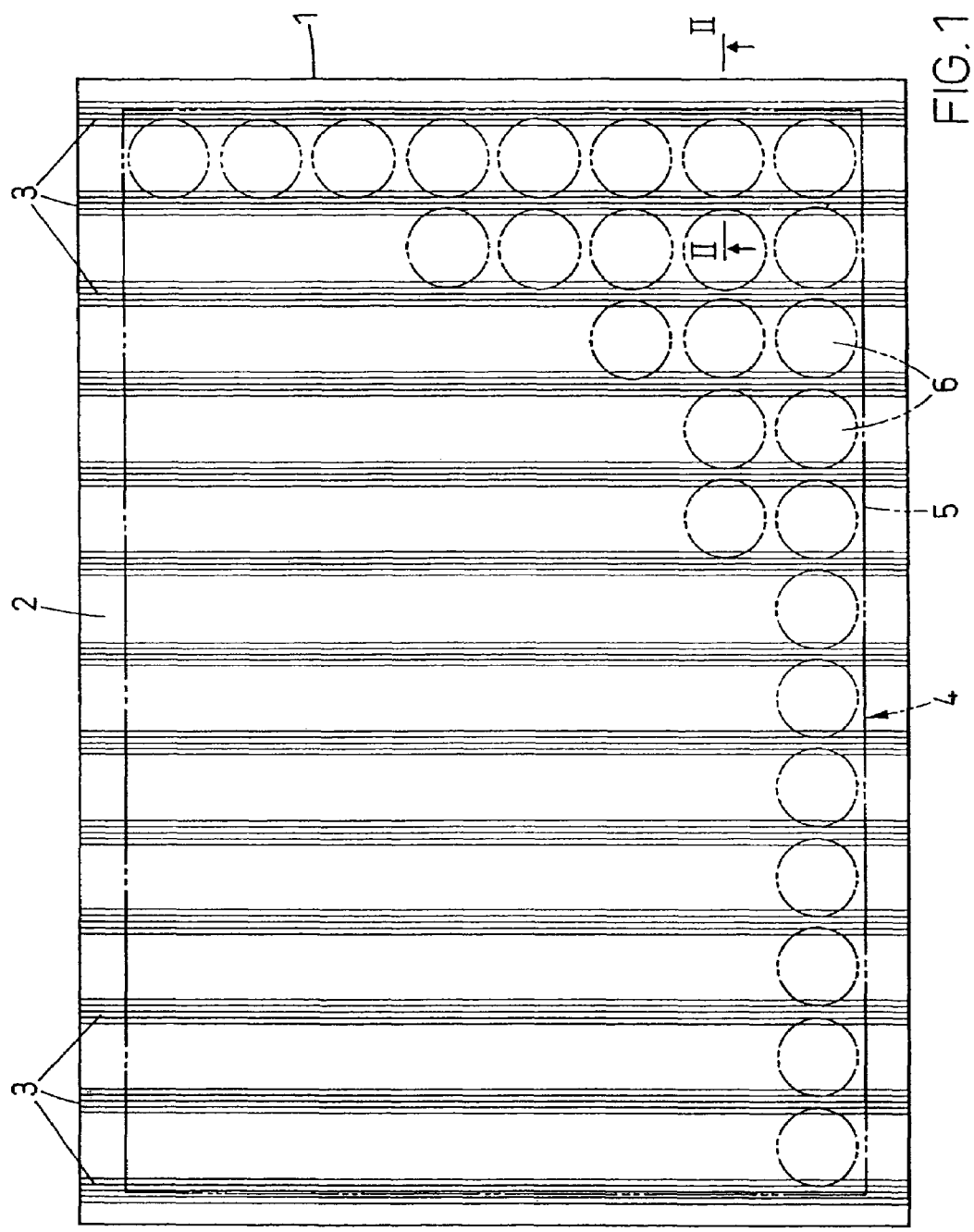
FIG. 1 shows a plan view of a waveguide plate according to the invention which can be an evanescent field sensor plate having an attachment or headpiece which is indicated by a dashed line and supplements it to form an arrangement of sample compartments or a complete microtitre plate with sample compartments or a complete waveguide plate system.

The process according to the invention will first be explained in more detail in connection with an evanescent field sensor plate, respectively a waveguide plate and its production. Here, an evanescent field sensor plate is understood as a waveguide plate making it possible, by illumination of one part of the surface, to create an evanescent field in which a sample to be analyzed may be arranged. Therefore, evanescent field sensor plates may for example serve the purposes of chemical analysis. Evanescent fields are nonradiating electromagnetic fields which fall off and vanish with increasing distance from the scattering surface at which they are generated. Such fields can arise in connection with spatial modulations at the electric field in the plane having periodicities smaller than one wavelength. The best-known example of such a modulation occurs at an interface between a dielectric and air when a light beam coming from the side of the dielectric has an angle of incidence larger than the critical angle.

Evanescent field sensor plates respectively waveguide plates have a transparent wave-guide layer from which the evanescent light leaves their surface, and interacts with bound molecules present there, for instance exciting their luminescence.

The plate according to the invention consists (FIGS. 1, 2, the diagrams are schematic and not to scale) of a glass substrate 1, for example of AF 45 from Schott DESAG, having dimensions of 102 mm×72 mm and a thickness of 0.7 mm, which carries on one side a 150 nm thick wave guide layer 2 comprising $Ta_2O_5$. Its refractive index at a wavelength of 633 nm is 2.11.

A plurality of parallel coupling grating strips 3 which are spaced apart and extend in parallel lines each over the entire width of the waveguide plate are present on the surface carrying the waveguide layer 2. The width of each of the coupling grating strips 3 is 0.5 mm. The grating period is □=360 nm, the groove/land ratio is about 1:1, and the grating depth is about 20 nm. The parameters defining the grating are each maintained very accurately over the total length of the coupling grating strip. Consequently, changes in the coupling angle □ at which a light beam directed from below through the glass substrate 1 at the coupling grating strip 3, in particular having a wavelength of about 633 nm, is coupled into the waveguide layer 2 with maximum coupling efficiency remains within very narrow limits. Along the lines of a coupling grating strip 3, the angle changes by not more than 0.05_/cm.

On the whole waveguide plate, the deviation of the coupling angle from the mean value, which is 2.31_ in the described example, is below 0.15_.

The surface of layer 2 is preferably provided with a coating consisting of an adhesion promoter layer, preferably of at least one chemical compound selected from the group of silanes, epoxides, functionalized, charged or polar polymers and self-organizing passive or functionalized mono-or multi-layers, and on top of it immobilized biological or biochemical or synthetic molecular recognition elements such as nucleic acids, antibodies, antigens, membrane receptors, and their ligands.

Figure 3:
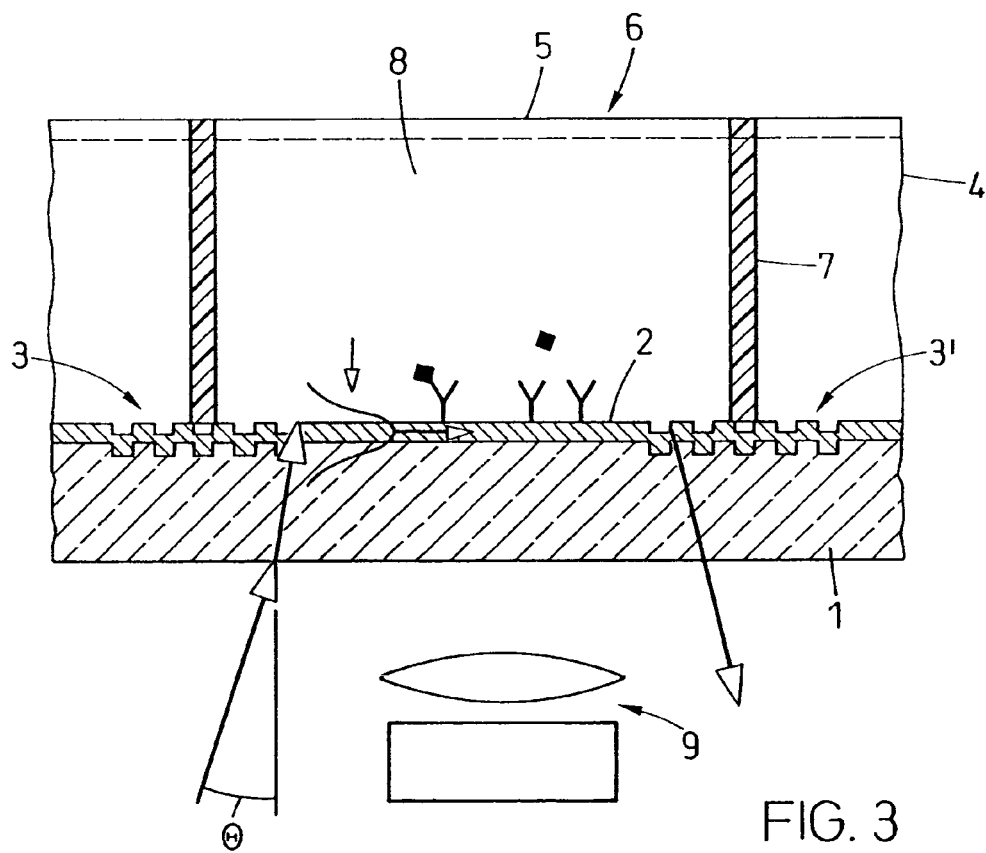

As shown in FIG. 3 and indicated in FIG. 1, the waveguide plate or evanescent field sensor plate is supplemented by a honeycomb-like attachment 4 of plastic to give an arrangement of sample compartments, preferably with the footprint of an industrial standard plate or to give a microtitre plate for use for chemical analysis, in particular of biological substances. The attachment has a cover plate 5 which is perforated by round openings 6 having a diameter of, for example, about 8 mm arranged in a regular array. At each of the openings 6, a tube section 7 which is open at the bottom, laterally bounds a cavity 8 and is tightly connected, for example adhesively bonded, at the lower end to the waveguide or evanescent field sensor plate 2.

On the other hand, in order to provide a waveguide plate enabling the conduction of fast analysis with low effort, a waveguide plate is provided, according to the invention, with a plate-like glass substrate (1), carrying a waveguiding layer (2), with at least one coupling grating on the surface carrying the waveguiding layer (2), which coupling grating is formed as a grating of lines with a period between 150 nm and 1000 nm, the extension of said grating being at least 5 cm with lines parallel to one another, wherein the coupling angle (□) varies by not more than 0.1_/cm along a line of said grating and wherein the absolute value of the deviation of the coupling angle (□) on said waveguide plate, from a predefined desired value, does not exceed 0.5_.

Additionally, a sensor platform and an arrangement of sample compartments, based on such a waveguide plate, shall be provided. These tasks are solved by the embodiments of sensor platforms and arrangements of sample compartments described below.

By means of the low limits (tolerances) of variations of the coupling angle, even in case of long grating lengths, it is possible to illuminate and read-out larger parts of the waveguide plate or of the sensor platform or of the arrangement of sample compartments simultaneously, i.e., to direct excitation light thereto and to detect the light emanating therefrom with one or more detectors. Also sequential exposures of different parts of the waveguide plate or of the sensor platform or of the arrangement of sample compartments are simplified, as a new optimization of their relative angular position and of the illumination unit is not required or at least significantly simplified.

In addition, the invention is based on the task to provide a method for the determination of one or more analytes in one or more samples, allowing for the analysis of a multitude of samples within short time, i.e., economically, and without the necessity of additional tedious system adjustments between sequential individual measurements. According to the invention, this is made possible by the arrangement of large gratings with high precision, especially of gratings with long lines parallel to each other, additionally providing freedom for the design of the geometrical arrangement of the gratings, which is simple and economic at the same time.

It is preferred that the extension of said coupling grating along said line is at least 1 cm. It is further preferred that the coupling angle (□) varies by not more than 0.05_/cm along said line.

Furthermore, it is preferred that the absolute value of the deviation of the coupling angle (□) from its average value on the waveguide plate does not exceed 0.3_, preferably not 0.15_.

Preferably, the refractive index of the waveguiding layer (2) is between 1.65 and 2.8. The waveguiding layer (2) can comprise, for example, $Ta_2O_5$, $Nb_2O_5$, $TiO_2$, $ZrO_2$, $Al_2O_3$, $SiO_2$—$TiO_2$, $HfD_2$, $Y_2O_3$, $SiONy$, $Si_3N_4$, $HfOxNy$, $AlOxNy$, $TiOxNy$, $MgF_2$ or $CaF_2$. The thickness of the waveguiding layer is preferably between 50 nm and 200 nm. It is advantageous if the groove/land ratio of the at least one coupling grating is between 0.3:1 and 3:1, preferably between 0.7:1 and 1.5:1. It is preferred additionally, that the grating depth of the at least one coupling grating is between 5 nm and 75 nm.

For many applications, it is advantageous, if the at least one coupling grating covers only a part of the surface of the waveguide plate, whereas a residual part of the surface of the waveguide plate is uncovered. Thereby, it is especially preferred, that the waveguide plate is provided with at least one coupling grating, which is formed as a coupling grating strip (3), with lines parallel to one another extending essentially over the whole width or length of the waveguide plate. Thereby, preferably several coupling gratings are arranged separate and parallel to each other.

The waveguide plate according to the invention can be modified in multiple ways without deviating from the basic idea of the invention. For example, also variable gratings, for example with a variable inter-grating line distance, can be manufactured and be provided as coupling gratings on the waveguide plate.

Also concerning the geometrical arrangement of the coupling gratings, there are further embodiments of the waveguide plate according to the invention, which can be advantageous for specific applications.

For example, several coupling gratings of a waveguide plate according to the invention must not be arranged in parallel to each other, but can also, for example, be arranged orthogonally (normal) to each other. Two or more coupling gratings can also be superimposed. For other specific applications, it is preferred that the coupling gratings are mono-diffractive. For specific applications, for example for the in coupling of excitation light of different wavelengths from multiple light sources into the waveguiding layer (2), however, it can be advantageous, if one or more coupling gratings are multi-diffractive.

In a preferred embodiment of the waveguide plate according to the invention a coupling grating covers essentially the whole surface of said waveguide plate. It has to be understood that, in this preferred embodiment, for example boundary areas on the waveguide plate and/or areas between larger parts provided with a coupling grating (with an area of the order of square centimeters) can be free from coupling gratings.

It is characteristic for a waveguide plate according to the invention, that coupling gratings arranged on said waveguide plate are operable to incouple excitation light from one or more light sources into the waveguiding layer (2) and/or to outcouple light guided in the waveguiding layer (2).

Another subject of the invention is a specific sensor platform with a waveguide plate according to any of the embodiments disclosed above, wherein biological or biochemical or synthetic recognition elements for the specific recognition and/or binding of one or more analytes and/or for the specific interaction with said analytes are immobilized directly on the waveguiding layer (2) or by means of an adhesion promoting layer additionally deposited on said waveguiding layer (2).

Thereby it is preferred that a multitude of similar or different biological or biochemical or synthetic recognition elements are immobilized in at least one array of discrete measurement areas directly on the waveguiding layer (2) or by means of an adhesion promoting layer additionally deposited on said waveguiding layer (2).

In the spirit of this invention, laterally separate ("discrete") measurement areas shall be defined by the closed area, which is occupied by the biological or biochemical or synthetic recognition elements immobilized thereon. These areas can have any geometry, for example the shape of spots, circles, rectangles, triangles, ellipses, or strips.

Similar to the waveguiding layer (2) and the glass substrate (1), an adhesion promoting layer, optionally deposited on the waveguiding layer (2), should be transparent at least in the spectral range of a launched excitation light and a luminescence light to be determined optionally. Thereby, said transparent spectral range can be between the ultraviolet and the infrared.

According to this invention, the term "luminescence" refers to the spontaneous emission of photons in the ultraviolet to infrared spectral range, after optical or not optical excitation, such as electrical or chemical or biochemical or thermal excitation. Chemiluminescence, bioluminescence, electroluminescence and, especially, fluorescence and phosphorescence are included in the term "luminescence".

The adhesion promoting layer should not exceed the penetration depth of the evanescent field from the waveguiding layer (2) into the medium located thereon. For example, the adhesion promoting layer can have a thickness of less than 200 nm, preferably of less than 20 nm.

An adhesion promoting layer deposited on the waveguiding layer (2) preferably comprises a chemical compound from the groups comprising silanes, functionalized silanes, epoxides, functionalized, charged or polar polymers and "self-organized passive or functionalized mono- or multilayers".

Preferred is an embodiment of a sensor platform according to the invention, wherein, as said biological or biochemical or synthetic recognition elements, components from the group formed by nucleic acids (such as DNA, RNA, oligonucleotides) and nucleic acid analogues (such as PNA, "peptide nucleic acids"), proteins, especially mono- and poly-clonal antibodies, peptides, enzymes, aptamers, synthetic peptide structures, soluable membrane-bound and from membrane isolated proteins, such as membrane receptors, their ligands, antigens for antibodies, "histidin-tag components" and their complex forming partners, cavities generated by chemical synthesis to host molecular imprints are immobilized directly on the waveguiding layer (2) or by means of an adhesion promoting layer additionally deposited on said waveguiding layer (2).

As the latter type of recognition elements, cavities have to be understood which are formed by a method described in the literature as "molecular imprinting". Following this method, the analyte or an analogue of the analyte, typically in organic solution, is encapsulated in a polymeric structure. It is then called an "imprint". Then, upon application of adequate reagents, the analyte or its analogue is dissolved from the polymeric structure again, leaving back an empty cavity. In a later analysis method, this empty cavity can be used as a binding site with high steric selectivity.

Also whole cells, cell components, cell membranes or their fragments can be immobilized as biochemical or biological recognition elements.

In many cases, the detection limit of an analytical method is limited from signals resulting from so-called nonspecific binding, which signals are caused by binding of the analyte or of other components applied for the determination of the analyte not only in the regions of the immobilized biological or biochemical or synthetic recognition elements, but to other regions free from these recognition elements, for example caused by hydrophobic adsorption or electrostatic interactions.

Therefore, it is advantageous when areas between the immobilized biological or biochemical or synthetic recognition elements on the waveguiding layer (2) or on the adhesion promoting layer additionally deposited on the waveguiding layer (2) and/or between the laterally separated measurements areas are "passivated", for a minimization of nonspecific binding of analytes or of tracer compounds for said analytes, wherein compounds which are "chemically neutral" towards the analyte are deposited in said intermittent areas, comprising preferably compounds from the groups comprising albumins, especially bovine serum albumin or human serum albumin, casein, nonspecific polyclonal or monoclonal, alien-characteristic or empirically nonspecific antibodies for an analyte to be determined (especially for immunoassays), detergents—such as Tween 20—, synthetic or natural lipids, fragmented natural or synthetic DNA, such as extracts from herring or salmon sperm, that do not hybridize with polynucleotides to be analyzed (especially for polynucleotide hybridization assays), or also comprising hydrophilic polymers, such as polyethylen glycols or dextranes.

It is preferred that a waveguide plate, respectively a sensor platform according to the invention is provided with an arrangement of preferably essentially closed sample compartments, for receiving one or more liquid samples to be analyzed. Subject of the invention thereby is an arrangement of one or more sample compartments, comprising a waveguide plate or a sensor platform according to the invention as a base plate and comprising a body combined with said base plate in such a way, that one or more spatial recesses are formed between the base plate and said body, for generation of one or more flow cells, each with at least one inlet and at least one outlet, which flow cells are fluidically sealed against each other.

Preferred is an arrangement of sample compartments in a 1- or 2-dimensional array, comprising a waveguide plate or a sensor platform according to the invention as a base plate and comprising a body combined with said base plate in such a way, that an array of spatial recesses is formed between the base plate and said body, for generation of an array of flow cells, each with at least one inlet and at least one outlet, which flow cells are fluidically sealed against each other.

In a specific embodiment of an arrangement of sample compartments according to the invention, spatial structures with the geometry of the footprint of the array of flow cells to be generated are formed on the waveguide plate or the sensor platform as the base plate.

It is preferred that recesses are formed in said body, for generation of the spatial recesses between the waveguide plate or the sensor platform as the base plate and said body to be combined with said base plate.

For an easier manufacturing, it can be advantageous, if the body to be combined with the waveguide plate or the sensor platform as the base plate is formed from several parts, wherein the combined parts of said body preferably form an irreversibly combined unit.

Thereby, it is preferred that the body combined with the waveguide plate or the sensor platform as the base plate is provided with means facilitating the combination of said body with the base plate.

An arrangement of sample compartments according to the invention can comprise, for example, 2–2000, preferably 2–400, still more preferably 2–100 flow cells.

It is preferred that the pitch (geometrical arrangement in rows and/or columns) of the inlets of the flow cells does correspond to the pitch (geometrical arrangement) of the wells of an industrial standard plate.

A specific embodiment of an arrangement of sample compartments according to the invention is related to, for example, 2 to 8 sample compartments in a column or, for example, 2 to 12 sample compartments in a row, which themselves are combined with a carrier ("meta-carrier") with the dimensions of industrial standard plates in such a way, that the pitch (geometrical arrangement in rows and/or columns) of the inlets of the flow cells does correspond to the pitch (geometrical arrangement) of the wells of an industrial standard plate.

It can be advantageous for many applications, for example in the course of nucleic acid hybridization assays with denaturation steps at elevated temperature (e.g. up to 80_C), if the arrangement of sample compartments according to the invention is closed with an additional covering top, for example a film, a membrane or a cover plate. Thereby, for example, an evaporation of liquid from the inlet and outlet openings of the sample compartments can be avoided.

In an arrangement of sample compartments according to the invention, the inner volume of each flow cell can typically be 0.1_1–1000_1, preferably 1_1–20_1.

It is preferred that the depth of the recesses between the waveguide plate or the sensor platform as the base plate and the body combined with said base plate is 1–1000_m, preferably 20–200_m.

The base areas of the recesses between the waveguide plate or the sensor platform as the base plate and the body combined with the base plate are typically 0.1 $mm^2$–200 $mm^2$, preferably 1 $mm^2$–100 $mm^2$ each, wherein the size of the recesses of an array can be equal or different, and wherein the base areas can have any geometry, preferably rectangular or polygonal or also other geometry.

It is characteristic for an arrangement of sample compartments according to the invention, that the materials of the body combined with the waveguide plate or the sensor platform, as the base plate, and of an optional additional covering top are selected from the group of formable, moldable or millable plastics, metals, silicates, such as glass, quarts or ceramics.

Further embodiments of adequate arrangements of sample compartments are described in PCT/EP 00/12668. In combination with a waveguide plate according to the invention, the arrangements of sample compartments described therein are another subject of this invention.

A further subject of the invention is an optical system for the determination of one or more luminescences with
at least one excitation light source
a waveguide plate or a sensor platform or an arrangement of sample compartments according to the invention, respectively, and
at least one detector for determination of the light emanating from the waveguide plate or the sensor platform and from measurements areas that might be located thereon.

In an embodiment of an optical system according to the invention, the excitation light is launched in a direct illumination or transmission illumination light configuration towards the measurement areas.

It is preferred that the detection of the luminescence light is performed in such a way that excitation light or luminescence light outcoupled by a coupling grating is detected as well.

In a preferred embodiment of the optical system, the excitation light emitted by the at least one light source is essentially parallel and is launched, at the resonance angle for incoupling by a coupling grating into the waveguiding layer (2), onto a coupling grating of the waveguide plate or the sensor platform or the arrangement of sample compartments.

As an "essentially parallel" light bundle, it shall be understood that its convergence or divergence are less than 1 degree. Correspondingly, "essentially orthogonal" or "essentially normal" shall mean a deviation from a corresponding orthogonal or normal direction by less than 1 degree.

For most embodiments (except for those based on the use of a polychromatic light source), it is also preferred that the excitation light is essentially monochromatic. As "essentially monochromatic" light shall be understood, that its bandwith is less than 1 nm.

Furthermore, it is preferred, that the excitation light is launched linearly polarized, for excitation of a $TE_0$- or $TM_0$-mode guided in the waveguiding layer (2).

For specific applications it is preferred that two or more light sources with similar or different emission wavelengths are used as excitation light sources. Preferably, these are coherent light sources.

Characteristic for a specific embodiment of the optical system according to the invention is, that the excitation light of at least one light source is expanded by an expansion optics to an essentially parallel ray bundle and directed on one or more measurement areas on a coupling grating, which is preferably performed under the resonance angle for incoupling into the waveguiding layer (2).

Characteristic for another specific embodiment is, that the excitation light from the at least one light source is divided, by means of one or, in case of several light sources, multiple diffractive optical elements, preferably Dammann gratings, or refractive optical elements, preferably micro-lens affays, into a multitude of individual beams, with as similar intensity as possible of the individual beams originating from a common light source, which individual beams are directed essentially in parallel to each other onto one or more coupling gratings and laterally separated measurement areas, which may be located on or aside of said coupling gratings.

For some applications, for example for the generation of expression profiles in the analytics of nucleic acids, it is preferred to use two or more light sources with similar or different emission wavelength as excitation light sources.

Thereby, the excitation light from two or more light sources can be launched simultaneously or sequentially from different directions onto two or more superimposed coupling gratings (as part of a specific embodiment of waveguide plate or sensor platform or arrangement of sample compartments according to the invention), which preferably have different periodicity.

Preferably at least one laterally resolving detector, for example from the group formed by CCD-cameras, CCD-chips, photodiode arrays, Avalanche diode arrays, multichannel plates and multichannel photomultipliers, is used for detection.

In an optical system according to any of the embodiments described above, optical components of the group comprising lenses or lens systems for the shaping of the transmitted light bundles, planar or curved mirrors for the deviation and optionally additional shaping of the light bundles, prisms for the deviation and optionally spectral separation of the light bundles, dichroic mirrors for the spectrally selective deviation of parts of the light bundles, neutral density filters for the regulation of the transmitted light intensity, optical filters or monochromators for the spectrally selective transmission of parts of the light bundles, or polarization selective elements for the selection of discrete polarization directions of the excitation or luminescence light can be located in the optical path between the one or more excitation light sources and a component of the group of components formed by a waveguide plate, a sensor platform, and an arrangement of sample compartments according to any of the embodiments described above, and/or in the optical path between said group of components and the one or more detectors.

Characteristic for a specific embodiment according to the invention is that the excitation light is launched in pulses with a duration between 1 fsec and 10 minutes, and that the emission light from the measurement areas is measured time-resolved.

Preferably, for referencing purposes, light signals of the group comprising excitation light at the location of the light sources or after expansion of the excitation light or after its multiplexing into individual beams, scattered light at the excitation wavelength or emission light at a wavelength different from the one used for analyte detection, from the location of the one or more laterally separated measurement areas, and light of the excitation wavelength outcoupled by a coupling grating aside of the measurement areas, are measured.

Thereby, it is of special advantage if the measurement areas for determination of the emission light and of the reference signal are identical.

Launching of the excitation light and detection of the emission light from the one or more measurement areas can be performed simultaneously or sequentially for one or more measurement areas.

Preferably, sequential excitation and detection is performed using movable optical components of the group comprising mirrors, deviating prisms, and dichroic mirrors.

Thereby, it is characteristic for a specific embodiment of an optical system according to the invention, that sequential excitation and detection is performed using an essentially focus and angle preserving scanner.

In another method for sequential excitation and detection of the emission from one or more measurement areas, the waveguide plate or sensor platform or arrangement of sample compartments is moved between steps of sequential excitation and detection.

Another subject of the invention is a method for the simultaneous qualitative and/or quantitative determination of a multitude of analytes, with a component of the group of components formed by a waveguide plate according to the invention and a sensor platform according to the invention and an arrangement of sample compartments according to the invention, and/or upon use of an optical system according to the invention, each according to any of the embodiments described above, wherein one or more liquid samples, to be analyzed for said one or more analytes, are brought into contact with the measurement areas on one of said components, exitation light is launched towards the measurement areas, and wherein at least one of (A) light emanating from the measurement areas and (B) optionally one or more luminescenses from the measurement areas brought into contact with said sample or said samples, resulting from the binding of one or more analytes to the biological or biochemical or synthetic recognition elements immobilized in said measurement areas or from the interaction between said analytes and said immobilized recognition elements, are measured, wherein said luminescences are generated in the near-field of the waveguiding layer (2).

Again, it is preferred that the excitation light is essentially monochromatic and launched essentially in parallel. It is especially advantageous, if the excitation light is launched linearly polarized, for excitation of a $TE_0$- or of a $TM_0$-mode guided in the waveguiding layer (2).

It is especially preferred for many embodiments of the method according to the invention if the excitation light from at least one light source is expanded as homogeneously as possible to an essentially parallel ray bundle by a beam expansion optics and directed onto the one or more measurement areas. Thereby, it is preferred that the diameter of the launched excitation light bundle is at least 2 mm, preferably at least 10 mm, in at least one direction.

Characteristic for another embodiment of the method according to the invention is, that the excitation light from the at least one light source is divided, by means of one, or in case of several light sources, by means of multiple diffractive optical elements, preferably Dammann gratings, or refractive optical elements, preferably micro-lens arrays, into a multitude of individual beams, with as similar intensity as possible of the individual beams originating from a common light source, which individual beams are directed essentially in parallel to each other onto laterally separated measurement areas.

In another embodiment of a method according to the invention it is preferred, that two or more coherent light sources with equal or different emission wavelength are used as excitation light sources.

Thereby, it is preferred that the excitation light for the measurement areas is coupled into the waveguiding layer (2) by means of one or more coupling grating.

The analysis method according to the invention allows for measuring (a) the isotropically emitted luminescence or (b) luminescence that is incoupled into the waveguiding layer (2) and outcoupled by a coupling grating, or for measuring luminescence comprising both parts (a) and (b) simultaneously.

Characteristic for the method, according to the invention, is also that for the generation of said luminescence, a luminescent dye or a luminescent nano-particle is used as a luminescence label, which can be excited and emits at a wavelength between 300 nm and 1100 nm.

Characteristic for a preferred embodiment of the method, according to the invention, is that the luminescence label is bound to the analyte or, in a competitive assay, to an analog of the analyte or, in a multi-step assay, to one of the binding partners of the immobilized biological or biochemical or synthetic recognition elements or to the biological or biochemical or synthetic recognition elements.

Characteristic for a specific embodiment is that a second or still more luminescence labels with similar or different excitation wavelength as the first luminescence label and with similar or different emission wavelength are used.

Thereby it is preferred that the second or still more luminescence labels can be excited at the same wavelength as the first luminescence label, but emit at different wavelengths than the first luminescence label.

On the other hand, it is advantageous for specific applications, if the excitation and emission spectra of the applied luminescence labels do not overlap or do overlap only little.

Characteristic for another specific embodiment of the analysis method according to the invention is, that charge transfer or optical energy transfer from a first luminescence label acting as a donor to a second luminescence label acting as an acceptor are used for analyte determination.

For example for a reduction of the contribution of background signals at the excitation wavelength to the detected measurement signal it can be advantageous, if the one or more luminescences and/or determinations of light signals at the excitation wavelength are determined with selectivity of polarization, wherein preferably the one or more luminescences are measured at a polarization that is different from the polarization of the excitation light.

Characteristic for another specific embodiment of an analysis method according to the invention is, that changes of the effective refractive index on the measurement areas are determined in addition to the determination of one or more luminescences.

This modification, as a combined method of a determination of the effective refractive index and of a laterally resolved luminescence measurement, allows, for example, for a detection of the binding of a ligand, as the analyte, to a biological or biochemical or synthetic recognition element, as the receptor, being immobilized in one or more measurement areas, by means of a change of the effective refractive index, and for a determination of a functional response of said ligand-receptor system, by means of a change of the luminescence from said measurement areas.

The receptor-ligand system can, for example, be a transmembrane receptor protein, with a ligand in a supplied sample binding to said transmembrane receptor protein. A functional response of this receptor-ligand system can, for example, be the opening of an ion channel, leading to a local change of pH or/and of the ion concentration. Such a local change can for example be detected by means of a luminescent dye with a pH dependent or/and ion-dependent luminescence intensity and/or spectral emission.

The analysis method according to the invention, according to any of the embodiments disclosed above, is suited for the simultaneous or sequential, quantitative and/or qualitative determination of one or more analytes from the group comprising antibodies or antigens, receptors or ligands, chelators or "histidin-tag components", oligonucleotides, DNA or RNA strands, DNA or RNA analogues, enzymes, enzyme cofactors or inhibitors, lectins and carbohydrates.

Characteristic for the method, according to the invention, is that the samples to be examined are, for example, aqueous solutions, such as, in especial, buffer solutions, naturally occurring body fluids, such as blood, serum, plasma, lymph or urine, or egg yolk or optically turbid liquids or tissue fluids or surface water or soil or plant extracts or bio- or synthesis broths, or are taken from biological tissue fragments or cell cultures or cell extracts.

Another subject of the invention is the use of a component from the group of components formed by a waveguide plate according to the invention, a sensor platform according to the invention, and an arrangement of sample compartments according to the invention, and/or of an optical system according to the invention, and/or of a method according to the invention, for quantitative and/or qualitative analyses for the determination of chemical, biochemical or biological analytes in screening methods in pharmaceutical research, combinatorial chemistry, clinical and preclinical development, for real-time binding studies and the determination of kinetic parameters in affinity screening and in research, for qualitative and quantitative analyte determinations, especially for DNA- and RNA analytics, for the generation of toxicity studies and the determination of gene or protein expression profiles and for the determination of antibodies, antigens, pathogens or bacteria in pharmaceutical product development and research, human and veterinary diagnostics, agrochemical product development and research, for patient stratification in pharmaceutical product development and for the therapeutic drug selection, for the determination of pathogens, nocuous agents and germs, especially of salmonella, prions, viruses and bacteria, in food and environmental analytics.

EXAMPLE 1

Figure 2:
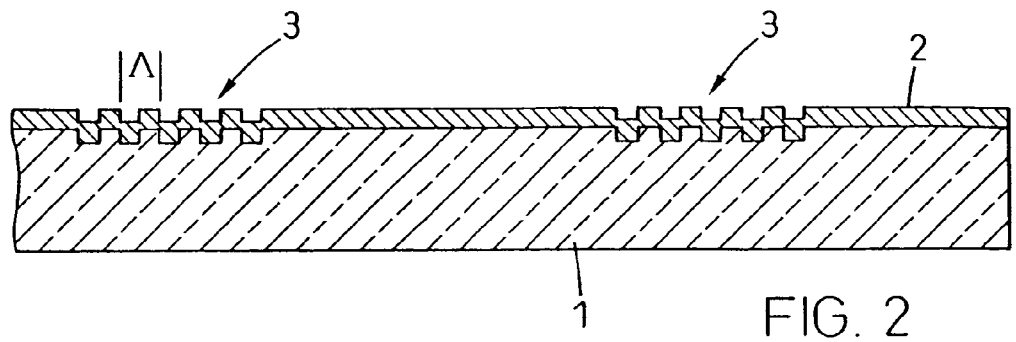
FIG. 2 shows a section along II—II in FIG. 1, FIG. 3 schematically shown the use of an arrangement of sample compartments or of a complete microtitre plate with a waveguide plate or a sensor platform (evanescent field sensor plate) according to the invention, as a boundary surface being part of the cavities of the sample compartments or the microtitre plate.

Design of a Waveguide Plate According to the Invention and Arrangement of Sample Compartments to be Formed by the Combination with said Waveguide Plate The waveguide plate according to the invention (FIGS. 1, 2 are schematically and not according to scale) comprises a glass substrate, for example of glass AF 45 from Schott DESAG, with dimensions of 102 mm×72 mm and a thickness of 0.7 mm, carrying on one surface a waveguiding layer 2 of $Ta_2O_5$ of 150 nm thickness. The refractive index is, dependent on the manufacturing method, for example 2.11 at 633 mn. Besides $Ta_2O_5$, also other materials are suited for the waveguiding layer, especially $Nb_2O_5$, $TiO_2$, $ZrO_2$, $Al_2O_3$, $SiO_2$—$TiO_2$, $HfO2$, $Y_2O_3$, $SiO_xN_y$, $Si_3N_4$, $HfO_xN_y$, $AlO_xN_y$, $TiO_xN_y$, $MgF_2$ or $CaF_2$.

On the surface carrying the waveguiding layer 2, several coupling grating strips 3 are arranged in parallel to and separate from each other, extending in parallel lines over the whole width of the waveguide plate. The width of each of the coupling grating strips 3 is 0.5 nun. The grating period is □=360 mn, the groove/land ratio is about 1:1, the grating depth about 20 mn. The parameters defining the grating are always fulfilled very precisely along the full length of the coupling grating strip. Thereby, changes of the coupling angle □, at which angle a light ray, directed from beneath towards the coupling grating strip 3 through the glass substrate 1, is coupled into the waveguiding layer 2 with maximum coupling efficiency, are kept in very narrow limits. Along the lines of a coupling grating strip 3, the coupling angle changes by not more (at maximum by) 0.05_/cm. On the whole of the coupling angle from the mean value, which is 2.31_ in the described example, is below 0.15_.

As shown in FIG. 3 and indicated in FIG. 1, the waveguide plate is accomplished by a honeycombed head piece 4, for example of plastics, to form an arrangement of sample compartments, for example with the footprint of an industrial standard plate.

If the content of a cavity 8 shall be examined for the concentration of certain molecules, an adjacent coupling grating strip 3 of the waveguide plate 2 is illuminated with light from an adequate light source under the coupling angle □, principally in a known matter, in this example from a He—Ne laser with light of a wavelength of 633 nm. The light guided through the waveguiding layer 2, forming the base (bottom) of the cavity 8, which is guided in this example, not limiting the general aspects of the invention, towards an adjacent coupling grating strip 3' and being outcoupled there again, does excite molecules in the cavity 8 to fluorescence which is detected by an optical system 9 and can then be analyzed. The high precision, within which the coupling angle □ can be guaranteed along the length of the coupling grating strip 3, allows for a simultaneous analysis of the cavities arranged along said coupling grating strip with high efficiency. The coupling angle □ deviating only little from the average value over the whole waveguide plate 2, for the analysis of the next row of cavities 8 a tedious optimization of said coupling angle is also not necessary.

EXAMPLE 2

Characterization of a Waveguide Plate According to the Invention

A waveguide plate according to Example I (waveguiding layer of $Ta_2O_5$, refractive index n=2.11 at 633 nm) is characterized. The waveguide plate is designed for use as a base plate for an arrangement of 96 sample compartments (provided as flowthrough cells) in a geometrical arrangement according to FIG. 1 (8 rows×12 columns of sample compartments). For the characterization of the physical properties of the waveguide plate, the following parameters shall be determined: (a) coupling angle and (b) the halfwidth of the resonance angle for maximum incoupling, (c) the lateral position ("x-position") for optimum incoupling on a coupling grating strip and (d) its halfwidth, (e) the incoupling efficiency, (f) the number and size of scattering centers per area unit of the region of the sample compartments, analysis of (g) the excitation light profile for the region of the sample compartments, (h) background luminescence at the wavelength of the luminescence measurement for an analyte determination to be performed later on.

In this example, the interval for the launching of excitation light and determination of the measurement light emanating from measurement positions for sample compartments in adjacent rows and columns is 9 mm.

Optical System for the Characterization

The optical system for the determination of the parameters for the characterization of a waveguide plate comprises three lasers, or laser diodes as alternative excitation light sources, with emission at 635 nm, 532 mn, and 492 mn. The excitation light from the different lasers is directed onto the coupling gratings of the waveguide plate by means of a system of lenses, apertures (for beam shaping) and mirrors. The last mirror in the excitation light path, before the light hitting the waveguide plate, is mounted on a goniometer (resolution 0.01' in this example), in order to allow for a precise adjustment of the coupling angle or for a deviation of the excitation light for the determination of the total excitation light intensity ($I_o$) launched onto the waveguide plate, and of the sum of the intensity of the reflected and immediately outcoupled excitation light ($I_r$, in parallel to the reflected light). The adjustment of the lateral position of the launching of the excitation light onto the waveguide plate (x: normal to the coupling grating strips; y: in parallel to the coupling grating strips) is performed by moving the waveguide plate by means of translational positioning elements (resolution 20 microns in this example).

The adjustment for maximum incoupling is performed by maximizing the signal of a photodiode (connected to an amplifier) measuring the light outcoupled at the next coupling grating, with respect to the direction of propagation of the light incoupled into the waveguiding layer. During that optimization, the intensities of the outcoupled light ($I_{out}$) are measured by the photodiode as a function of the incoupling angle (defined as the angle with respect to the normal of the waveguide plate), within an adjustment range and with a variable resolution, which can both be defined by the user. The optimum values for maximum incoupling and the halfwidths of the coupling curves (resonance curves) are then determined from these intensity profiles.

For the determination of the relative incoupling efficiency (e), the intensity of the undiffracted light ($I_{tr}$), transmitted through the waveguide plate, the intensity of the launched excitation light ($I_o$), and of the sum ($I_r$) of the reflected light and of the light outcoupled at the incoupling grating (not distinguishable from the reflected light as being outcoupled in parallel to the reflected light) are measured with calibrated photodiodes (connected to amplifiers). The incoupling efficiency is determined as the ratio $(I_o-I_{tr}-I_r)/I_o$.

For the determination of the other characterization parameters (f) to (h), the light emanating from the range of interest on the waveguide plate is imaged onto a laterally resolving detector, such as a camera or a CCD-chip, by means of an imaging system (combination of objective lenses). The measurement for the determination of the parameters (f) and (g) is again performed at the actual excitation wavelength (using neutral density filters for attenuation of the light intensity if necessary, but without use of spectrally selective filters), whereas the background luminescence (h) is determined upon using an adequate interference filter, which is mounted in a rotatable filter wheel in the optical path for the collection of this measurement light.

For the determination of the (f) number and size of scattering centers, first an average value of the signal intensities (from all pixels) of the whole area of interest is determined from the image (taken at the excitation wavelength). Thereby, it has to be taken care that the region of the coupling grating or areas immediately adjacent to the coupling grating are not taken into account in this averaging process, and, of course, reflections reaching the detector have to be avoided. Then a threshold intensity is defined, which is significantly higher than the upper limit of the statistical variation around the average value (definable by the user, for example average value+its tenfold standard deviation). All pixel signals above this threshold value are attributed to scattering centers, and a table is generated, how many of these pixels in a (2-dimensional) continuous area have signals above this threshold value (size of the scattering centers). The complete analysis for scattering centers is then provided in the form of a "histogram" with the number of scattering centers as a function of their size.

For the (g) determination of an excitation light profile of an area of interest on the waveguide plate, line profiles of the recorded pixel values of strip-like image sections of the corresponding areas on the waveguide plate (in y-direction, in parallel to the, grating lines) are generated. Based on these line profiles, it can be determined if, for example, no or reduced light incoupling does occur, because of defects of the coupling gratings at different sites, or if the propagation of the incoupled, guided light is interrupted or impaired (because of defects localized at sites further down in x-direction). Threshold values for the homogeneity (in y-direction; e.g. amount of the variation or relative deviation from the measured average value) of the measured intensity can be defined, the waveguide plate being discarded upon the occasion of their exceeding.

As mentioned, the background luminescence is determined upon using an adequate spectral filter for the actual luminescence wavelength of interest. Localized luminescent contaminations can be determined, for example in a manner similar to the analysis of scattering centers, and also integral luminescence intensities of all pixel values relevant for the analysis of the whole area of interest can be determined. Preferably, the measured values are corrected or referenced, respectively, with the available excitation light intensities, in order to allow for an empiric comparison between comparable waveguide plates. Similar as for all parameters mentioned above, again threshold values can be defined, a waveguide plate being discarded upon an exceeding or failing below these threshold values.

Preferably, all steps of the characterization of a waveguide plate are performed completely automatically resp. computer-controlled. It is especially preferred that a protocol is generated, comprising, for example, tables and optionally graphic representations of the determined parameters. Preferably, the grading and categorization of the characterized waveguide plates is performed in an automated manner as well.

As an example for a partial result of the characterization of a waveguide plate according to the invention, the average values of the determined coupling angles for excitation at 635 nm and at 532 nm, measured along a coupling grating strip ("column"; averages of 8 measurement positions), and the maximum deviations ($_{max-}$, $_{max+}$) along a coupling grating strip ("column," distance between first and last measurement position of a column: 63 mm) are summarized in the following table.

Along all coupling grating strips (columns), the variation of the coupling angle for both wavelengths is below 0.1'/cm; on the whole from the average value is below 0.5_.

TABLE 1

Average coupling angles on adjacent coupling grating strips ("columns") and maximum positive and negative deviation of the coupling angle along one coupling grating strip. Last row: Average values and maximum deviations on the whole waveguide plate.

| Column (coupling grating strip) No. | Excitation: 635 nm Coupling angle [_] | | | Excitation: 532 nm Coupling angle [_] | | |
|---|---|---|---|---|---|---|
| | AVG | $_{-max-}$ | $_{-max+}$ | AVG | $_{-max+}$ | $_{-max+}$ |
| | −13.39 | −0.15 | +0.28 | 11.72 | −0.22 | +0.27 |
| | −13.34 | −0.15 | +0.23 | 11.77 | −0.20 | +0.31 |
| | −13.26 | −0.13 | +0.22 | 11.84 | −0.17 | +0.26 |
| | −13.21 | −0.11 | +0.21 | 11.94 | −0.22 | +0.28 |
| | −13.13 | −0.17 | +0.29 | 12.00 | −0.19 | +0.31 |
| | −13.10 | −0.18 | +0.28 | 12.03 | −0.20 | +0.30 |
| 7 | −13.08 | −0.18 | +0.27 | 12.07 | −0.21 | +0.27 |
| | −13.07 | −0.16 | +0.24 | 12.09 | −0.23 | +0.34 |
| | −13.06 | −0.19 | +0.29 | 12.08 | −0.21 | +0.27 |
| | −13.06 | −0.16 | +0.27 | 12.07 | −0.21 | +0.28 |
| | −13.08 | −0.16 | +0.28 | 12.05 | −0.19 | +0.28 |
| | −13.10 | −0.15 | +0.28 | 12.03 | −0.20 | +0.32 |
| Whole plate | −13.15 | −0.39 | +0.38 | 11.98 | −0.48 | +0.45 |

If it is intended to investigate the contents of a cavity 8, for instance an analyte such as blood, serum, urine, saliva, or a solution containing a drug candidate, with respect to the concentration of specific molecules, an adjacent coupling grating 3 of the evanescent field sensor plate 2 is exposed in a manner known per se to a suitable light source at the coupling angle _, the light having a specific wavelength, in the example to light with a wavelength of 633 nm, by means of a He—Ne laser. The light is conducted through the layer 2 forming the bottom of the of the cavity 8 to the adjacent coupling grating 3', and there coupled back out. The evanescent light stimulates flourescence in molecules in the cavity 8 which are bound to recognition elements, which fluorescence is recorded by an optical system 9 and then analyzed. The high precision with which the coupling angle_ is preserved over the length of the coupling grating 3 permits a simultaneous and highly efficient examination of the cavities arranged along the same. Since over the entire evanescent field sensor plate 2, the coupling angle_ departs but slightly from the mean value, no laborious optimization of this angle is required even when examining the next row of cavities 8. As an alternative or in addition to evaluating the fluorescence, one can also record changes in the refractive index produced at the bottom of cavity 8 by the binding of molecules to the recognition elements.

Figure 4A:
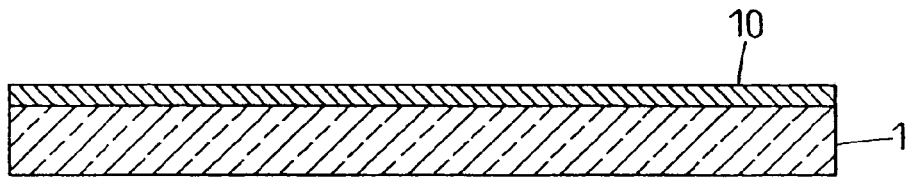
FIG. 4a–e show different steps in the production of a waveguide plate according to the invention, FIG. 5 schematically shows the setup used for exposing the photoresist layer during the production of the waveguide plate according to the invention.

As shown schematically in FIGS. 4a–e, to produce the transparent layer 2, one first applies a photoresist, e.g. AZ1518, diluted 1:4 with AZ1500, both of Clariant, at 1300 rpm to the substrate 1 and then bakes for 30 min at 90_C in an oven, whereupon Aquatar of the same manufacturer is applied at 1400 rpm and once again baked for 15 min at 90_C in the oven. The photoresist layer 10 thus produced has a thickness of less than 200 nm, as a rule of about 150 nm, so that interfering standing waves will not develop in it. The reflectivity is below 1%, so that interfering reflections which could lead to the development of Newton's rings are also practically excluded (FIG. 4*a*).

Figure 5:
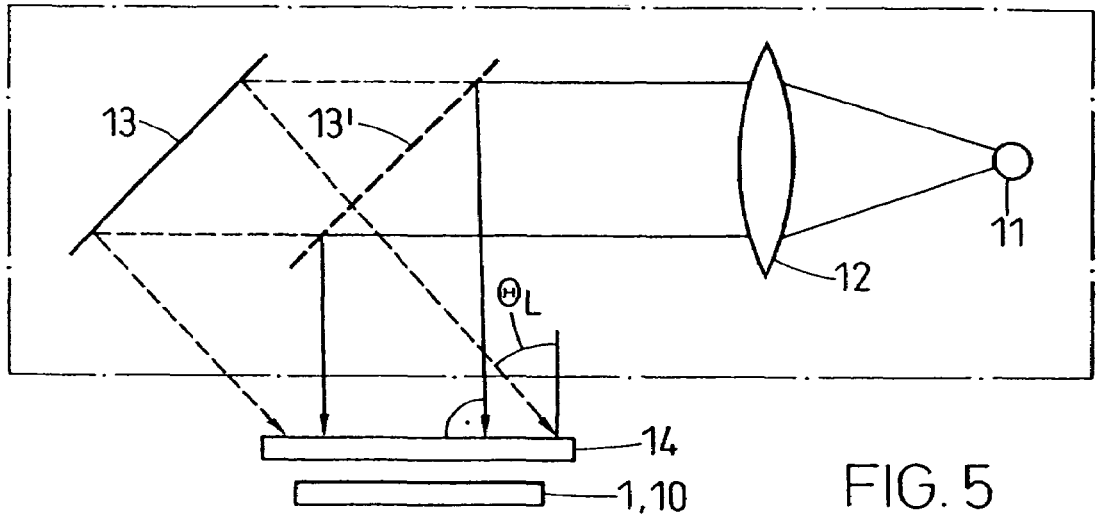

In a subsequent step, the photoresist layer 10 is exposed for 70 sec. For this purpose, the glass substrate 1 is introduced into a setup according to FIG. 5, a mask aligner MA4 from Stüss, Munich, which comprises a modified mercury vapour lamp 11 having a modified down-circuit optical system 12 and deflecting mirror 13. The optical system 12 comprises a bandpass filter which, for example, filters out the I-line at a wavelength of 365 nm, and a polarizer, which preferably produces s-polarization. To improve the parallelism of the beams, the fly's eye is removed from the beam path and a lamp with as small an arc as possible is used and is positioned as far away from the substrate as possible.

Figure 7A:
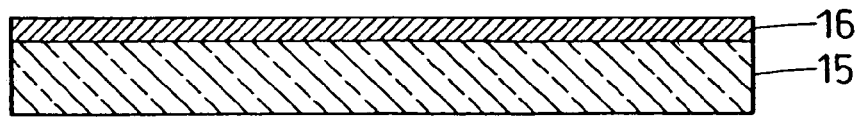
Figure 7B:
Figure 7C:
Figure 7D:
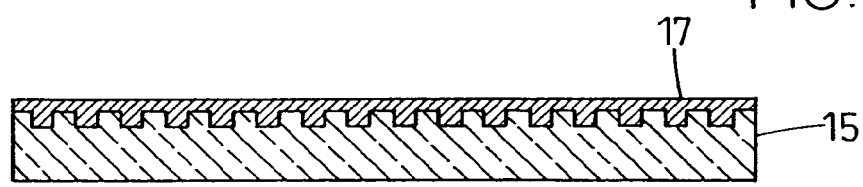
Figure 7E:
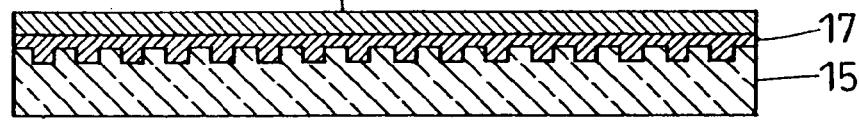
Figure 7F:
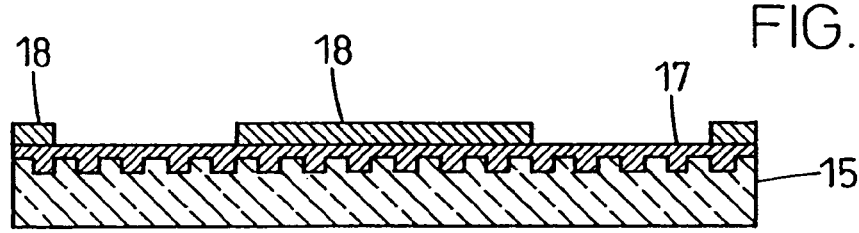
Figure 7G:
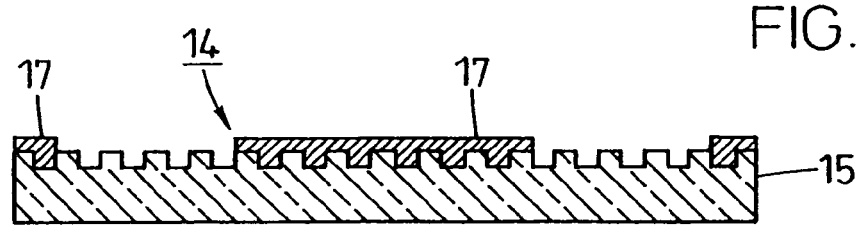

The exposure is performed through a phase mask 14. It comprises a substrate of a transparent material, in the example quartz, with a diffraction grating which carries a structured layer of nontransparent material, in the example chromium, which in this case is interrupted by strips following one another at regular intervals. Phase masks of this type and are manufactured approximately as follows:

A quartz substrate 15 is covered with a photoresist layer 16 (FIG. 7*a*) and the latter is exposed to light by the two-beam interference method and developed (FIG. 7*b*). Such structure can be obtained from Ibsen in Farum (Denmark). Thereafter, a diffraction grating is produced on the surface of the quartz substrate 15 by etching and subsequent removal of the photoresist over the whole area (FIG. 7*c*). Said surface is then completely covered with a chromium layer 17 (FIG. 7*d*). A continuous photoresist layer 18 is then applied to the chromium layer 17 (FIG. 7*e*) and exposed through a mask structured by inscribing by-means of electron or laser beams. The photoresist is then developed (FIG. 7*f*) and the chromium layer 17 is removed by etching from the parts not covered by photoresist. Finally, the residues of the photoresist layer 18 are removed to complete the phase mask 14 (FIG. 7*g*). The structure of the mask thus determines which parts of the phase mask are transparent.

Figure 6:
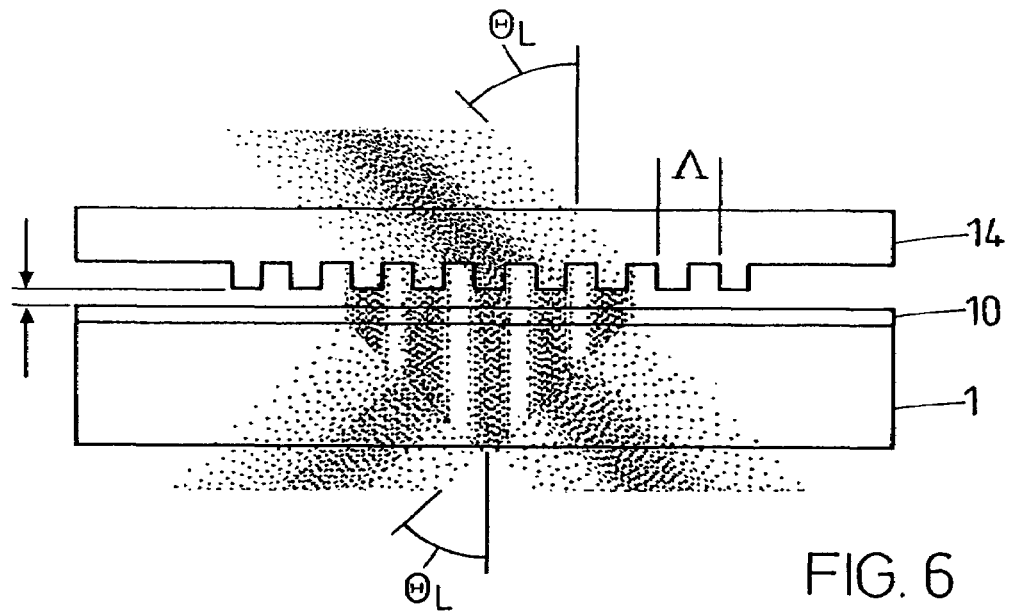
FIG. 6 shows the phase mask and the glass substrate with the photoresist layer under exposure and FIG. 7a–g show different steps in the production of a phase mask for the production of a waveguide plate according to the invention.

The substrate 1 is arranged underneath the phase mask 14 in such a way that the photoresist layer 10 is in vacuum contact with said phase mask. The upper side of the phase mask 14 is exposed at an angle which corresponds approximately to the Lithrow angle $\square_L$ at which the angle of incidence is equal to the angle of first order diffraction, in particular deviates by not more than 10_, preferably not more than 5_, from that angle. Under these conditions, a pronounced diffraction pattern whose structure corresponds to that of the grating of the phase mask 14 forms in the vicinity below the transparent regions of the phase mask 14 (FIG. 6). Alternatively, the phase mask 14 can also be exposed at an angle which approximately corresponds to a right angle, in particular deviates therefrom by not more than 10_, preferably not more than 5_ (deflecting mirror 131 shown as a dashed line). In this case, the diffraction pattern in the vicinity of the phase mask 14 has half the period of the grating thereof.

Figure 4B:
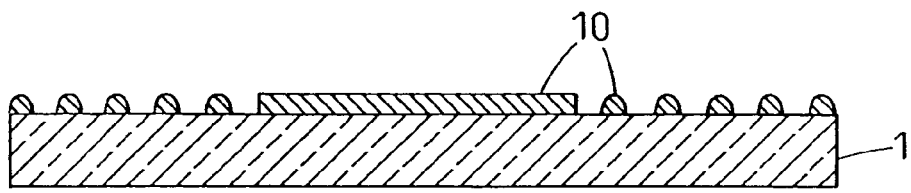
Figure 4C:
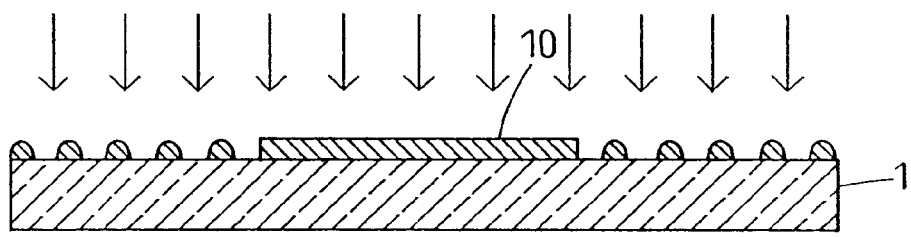
Figure 4D:

After exposure the Aquatar layer is removed by washing with deionized water, and the photoresist is then developed (FIG. 4*b*). Those parts of the surface of substrate 1 which are not covered with photoresist are then etched with Ar and CHClF2 at a pressure of 0.2 mbar in a parallel-plate reactor with capacitive excitation of the plasma at 13.6 MHz and an RF power of 50 W. The etch depth is 20 nm. The photoresist is then removed. For this purpose, it is first subjected to reactive ion etching for 60 s in an oxygen plasma at a pressure of 0.2 mbar and an RF power of 50 W, then detached with Remover AZ100, Deconex, and deionized water (FIG. 4*d*).

Figure 4E:
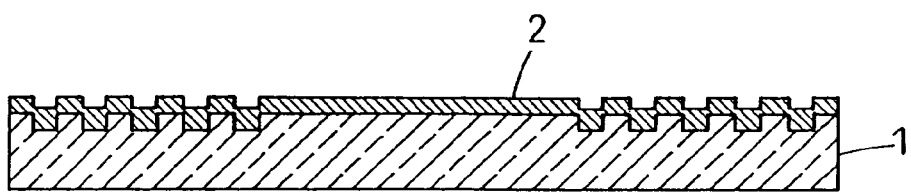

Finally the layer 2 is applied by reactive pulsed DC magnetron sputtering or by DC magnetron sputtering superimposed with an AC frequency between 1 kHz and 1 MHz, in a Balzers MSP1000 unit, similarly as described in EP-A-0 508 359 (FIG. 4*e*). This step is carried out in an Ar—O2 atmosphere at a pressure of 3.7_ bar. The target material is tantalum. Finally, the evanescent field sensor plate or waveguide plate respectively is cut to its final size by wafer sawing.

Particularly on account of exposure through a phase mask that can be reused practically as often as desired, the process described permits the production of elements with grating structures, particularly diffractive coupling gratings, in large numbers and in a simple manner. The fact that the phase mask is structured by the two-beam interference method also implies that large defect-free grating, structures having surface areas of 10 cm$^2$ and more can be produced on it with high precision, whereas other structuring methods such as electron beam writing are not suitable for this purpose owing to their virtually unavoidable stitching errors. Therefore, large optical, elements with large-area gratings of high quality and uniformity can be produced, not only as final products but also as semifinished plates which by wafer sawing, scribing and breaking or laser cutting can then be separated into smaller final products which thus can be produced very economically and in high quality.

Evanescent field sensor plates or waveguide plates respectively can of course also be produced in geometries and optical properties corresponding to other standards or requirements. Thus, another evanescent field sensor plate or waveguide plate respectively can have dimensions of 57 mm×14 mm×0.7 mm and be provided with two strip-shaped coupling gratings having a width of 0.5 mm each which are symmetrically arranged in parallel with the long sides, and have a mutual distance of 9 mm. The grating period A=318 nm, the grating depth 12 nm, while otherwise the properties of the layer and coupling gratings are the same as in the first example. In this case the coupling angle $\square$=−12.14_ at a wavelength of 633 nm, varying parallel to the lines by at most 0.15_/cm. The deviation from a mean value remains below 0.05_ everywhere on the evanescent field sensor plate or waveguide plate respectively. For the production of a semifinished plate from which the individual evanescent field sensor plates or waveguide plates respectively are then obtained by wafer sawing, a phase mask is employed which measures 150 mm×150 mm and has a region with a grating of grating period 318 nm measuring 115 mm×115 mm. The regions corresponding to the coupling gratings are bare while the remaining portion of the grating is again masked by a nontransparent layer, particularly a chromium layer. Otherwise the production proceeds as described above.

A further example is an evanescent field sensor plate or waveguide plate respectively measuring 75 mm×113.5 mm 0.7 mm which as to its basic features essentially corresponds to FIG. 1, and which bears 13 strip-shaped coupling gratings each 0.5 mm wide which are parallel to the broadside and have distances between neighboring strips of 8.5 mm each. Layer and grating properties correspond to those of the second example. The coupling angle $\square$=−11.48_ at a wavelength of 633 nm, varying parallel to the lines by at most 0.05_/cm. Over the entire evanescent field sensor plate or waveguide plate respectively it departs from a mean value by at most 0.4_. The evanescent field sensor plate or waveguide plate respectively can be expanded to a microtitre plate or waveguide plate respectively with 8×12 cavities by adding a suitable top portion.

Apart from the embodiments of optical elements having grating structures produced by the process according to the invention and used in chemical analysis, as portrayed above, embodiments for applications in communications technology are particularly pertinent. Such elements are suited above all as highly efficient optical couplers such as those employed in fibre-optic networks.

Figure 8A:
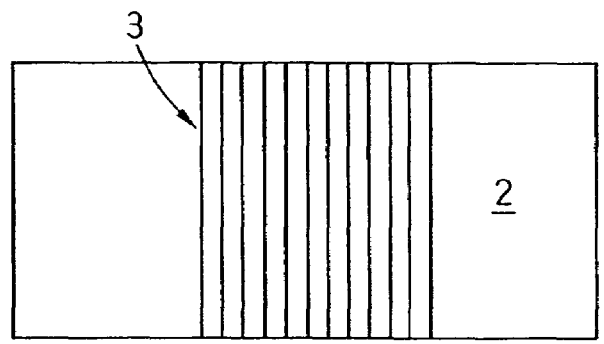
FIG. 8a schematically shows a plan view of a first embodiment of an optical coupler for communications technology according to the invention, FIG. 8b schematically shows a central section through the coupler according to FIG. 8a, FIG. 9a schematically shows the reflectivity of the coupler according to the first embodiment.
Figure 8B:
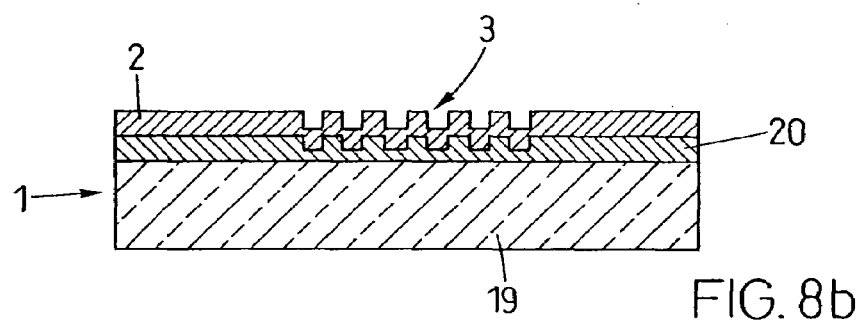
Figure 9A:
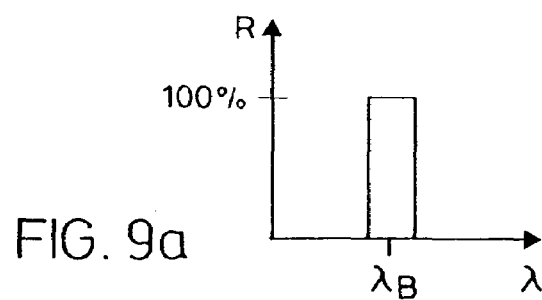
FIG. 9b–d shows diagrams showing the selection of a wave-length by the coupler according to the first embodiment.
Figure 9B:
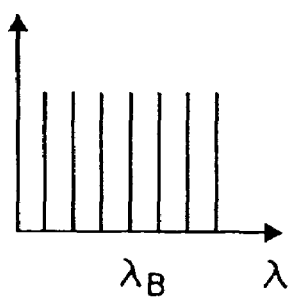
Figure 9C:
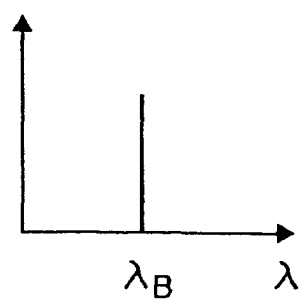
Figure 9D:
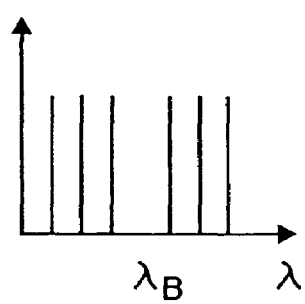

A first example of such a coupler is represented in FIGS. 8a and 8b. On a substrate 1 consisting of a glass plate 19 and a layer 20 of transparent material, a coupling grating 3 formed as a line grating of constant grating period is arranged. The layer 20 is covered by a transparent layer 2, consisting for instance of $Ta_2O_5$. Layer 2 acts as a waveguide. The coupling grating 3 reflects light of a particular wavelength $X_B$ according to the wavelength-dependent reflectivity R schematically represented in FIG. 9a, while incident light of all other wavelengths is transmitted. This is shown in FIGS. 9b–d, where FIG. 9a shows the incident wavelengths, FIG. 9b the reflected wavelength $\square_B$, and FIG. 9c the transmitted wavelengths. Using the coupler it is thus possible to filter out a particular wavelength, for instance in a fibre-optic network using wavelength multiplexing. Thanks to the high grating quality, the full width at half maximum of the reflectivity R as a function of wavelength is very small. Hence even with wavelengths very closely spaced, it is possible to highly efficiently separate a wavelength.

Figure 10:
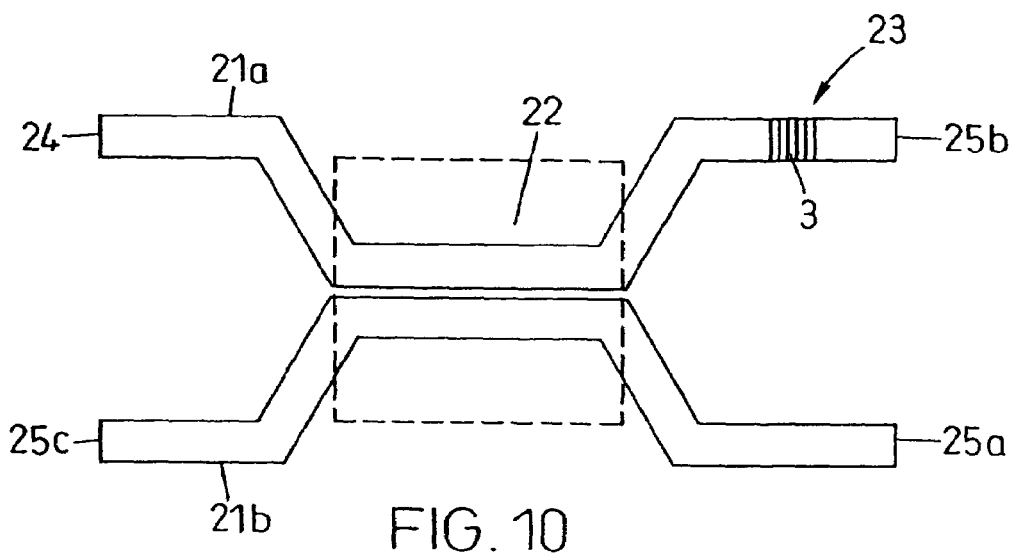
FIG. 10 shows an arrangement with a coupler according to the first embodiment, FIG. 11a schematically shows a plan view of a second embodiment of an optical coupler for communications technology according to the invention, FIG. 11b schematically shows a central section through the coupler according to FIG. 11a, FIG. 12 shows an arrangement with a coupler according to the second embodiment, FIG. 13a schematically shows a plan view of a third embodiment of an optical coupler for communications technology according to the invention, FIG. 13b schematically shows a central section through the coupler according to FIG. 13a, FIG. 14 shows a device for monitoring and stabilizing the wavelength of a light beam emitted by a laser which comprises a coupler according to the third embodiment.

An example for the use of such a coupler is shown in FIG. 10. Two parallel stripe waveguides 21a, b of known structure are running parallel at a very small mutual distance in a coupling region 22, in such a way that 50% of the light conducted in the first stripe waveguide 21a is transferred to the second stripe waveguide 21b, and vice versa. In the final segment of the first stripe waveguide 21a, a coupler 23 with a coupling grating 3 according to FIGS. 8a and b is incorporated which selectively reflects light having a wavelength $\square 3$.

When signals having wavelengths $\square_1$, $\square_2$, $\square_3$, $\square_4$ etc. are fed into the first stripe waveguide 21a at an input 24, then on one hand 50% of all signals in the coupling region 22 are transferred to the second stripe waveguide 21b where they are conducted to a first output 25a, while the signals remaining in the first stripe waveguide 21a are conducted to a second output 25b, except for the signal of wavelength X3 corresponding to the $\square_B$ according to FIGS. 9a–d which is reflected at the coupler 23 so that in the coupling region 22, 50% of its intensity transfer into the second stripe waveguide 21b where the signal is conducted in a direction opposite to that of the signals transferred directly from the first stripe waveguide 21a, and reaches a third output 25c where finally it has been isolated and can be further processed. The signals of outputs 25a and b can be recombined to a signal differing from the original one only by a 50% attenuation of the signal with wavelength $\square 3$.

The coupler 23 can be completely integrated into the first stripe waveguide 21a, in such a way that this has the same structure as coupler 23 and this coupler forms a single part with the first stripe waveguide 21a. The only distinction of coupler 23 is then its bearing the coupling grating 3.

Figure 11A:
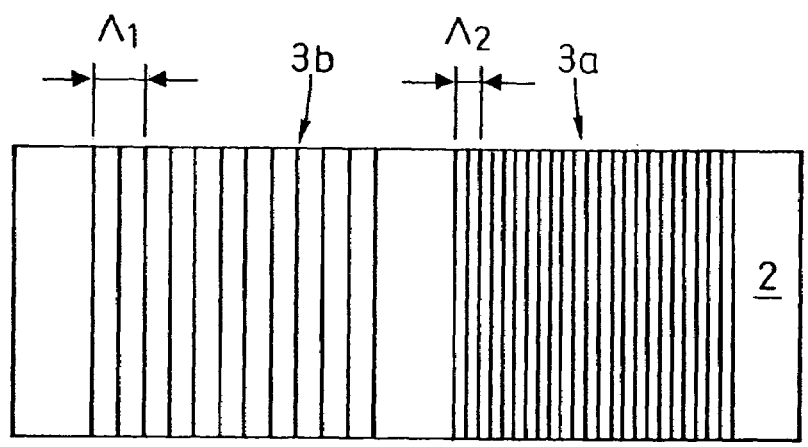
Figure 11B:
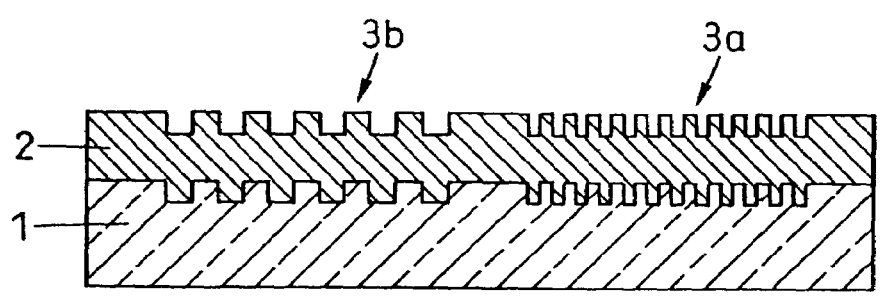

A second example of a coupler is represented in FIGS. 11a and b. In a longitudinal direction on top of a rectangular substrate 1 of glass, for instance Schott DESAG AF 45 with a refractive index of 1.52, two coupling gratings, an input coupling grating 3a and an output coupling grating 3b, are arranged consecutively at a mutual distance, each extending over the full width of the coupler. The input coupling grating 3a has a grating period of $\square_1$=981 nm and a grating depth of 6 nm, the output coupling grating 3b has a grating period of $\square_2$=1350 nm and a grating depth of 12 nm. The upper side of substrate 1 is covered by a continuous transparent layer 2 consisting of $Ta_2O_5$ and having a refractive index of 2.1. Its thickness is 400 nm.

Figure 12:
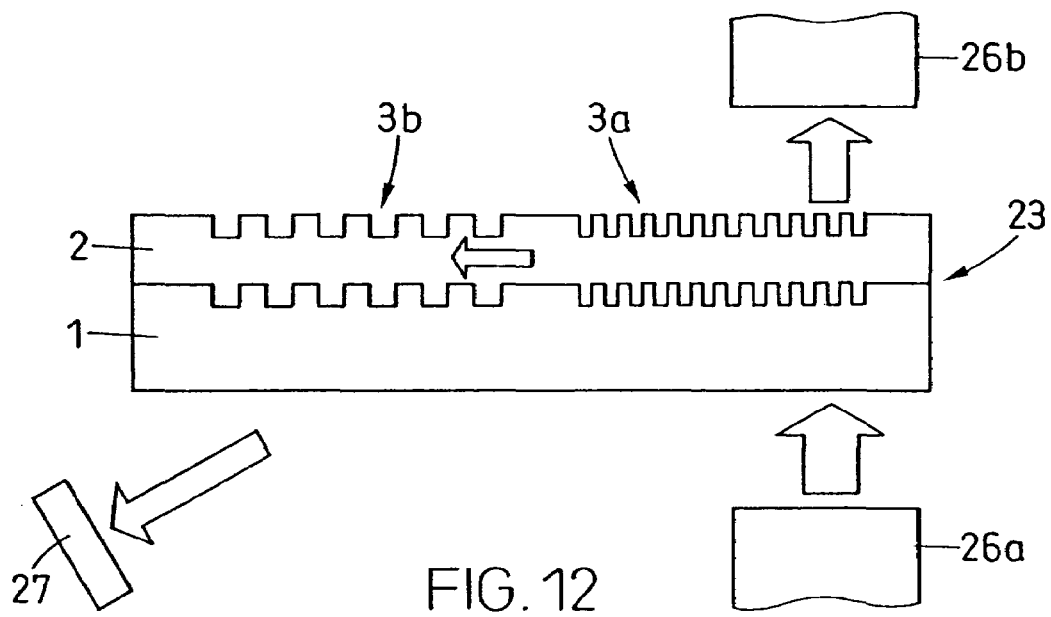

The coupler can be used as a drop filter monitoring and stabilising the intensity of a light beam, for instance a line of a multimode laser. To this end (FIG. 12), the coupler 23 described above is so arranged between the ends of a first optical fiber 26a and a second optical fiber 26b arranged in the continuation of the former that the input coupling grating 3a faces the end of the latter while the former faces the bottom side of coupler 23. The light supplied by the first optical fibre 26a passes through the part of the coupler 23 carrying the input coupling grating 3a while a fraction of the light of the 1550 nm line corresponding to less than 0.01% of its intensity is coupled into the layer 2 by said grating. At the output coupling grating 3b, light is coupled out at an angle of 30_ and reaches an appropriately disposed photodetector the output signal of which is a measure of intensity of the monitored line. Owing to the high precision of the input coupling grating 3a, the input coupling is highly wavelength-sensitive, the full width at half maximum of the intensity distribution being a mere 0.01 nm, so that a specific monitoring of a single wavelength is possible even where the wavelengths are closely spaced, as desired in wavelength multiplexing in the interest of a high transmission capacity.

Figure 13A:
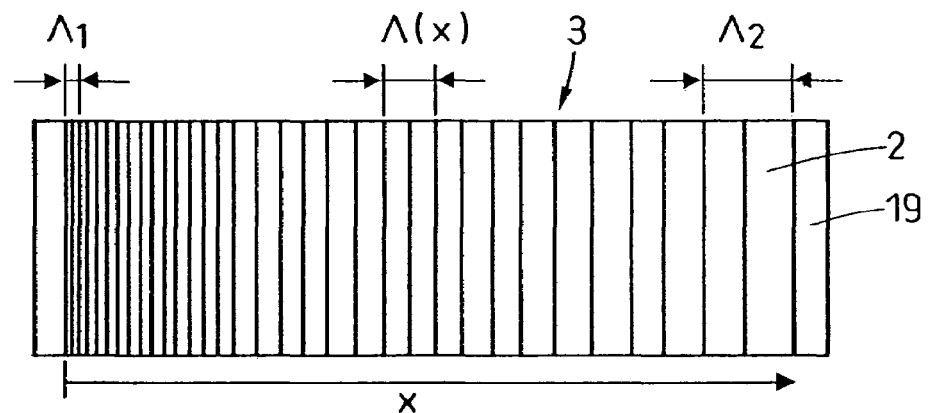
Figure 13B:
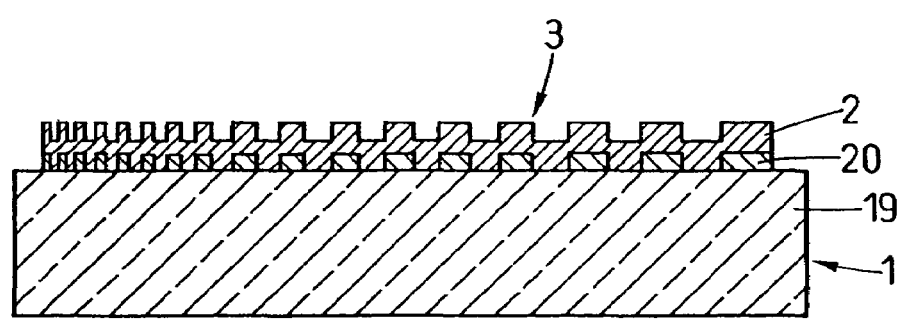

A third example of an optical coupler according to the invention is represented in FIGS. 13a and b. A rectangular substrate 1 consists of a glass plate 19 with a refractive index of 1.586 and a transparent layer 20 of $TiO_2$ with a refractive index of 2.4 covering the upper face of this glass plate in a thickness of 285 nm. The upper face bears a coupling grating 3 occupying its full width which has been produced by removing layer 20 completely in a pattern of lines, and is covered by a further transparent layer 2 consisting of $MgF_2$ which is 342 nm thick and has a refractive index of 1.38. The grating depth thus corresponds to the thickness of layer 20, and is 285 nm. The grating period $\square_{(x)}$ varies linearly in a direction normal to the grating lines, increasing from $\square_1$=970 nm to $\square_2$=977 nm.

When producing the coupler, layers 20 and 2 can be applied as described in connection with the first example of an evanescent field sensor plate or waveguide plate respectively. Production of the coupling grating 3 after application of the layer 20 also occurs as described there. In this operation, a phase mask is used whose grating varies appropriately, hence linearly in the present case. Such phase masks can be produced by appropriately bending a flexible master copy and applying a grating structure using the two-beam interference method. The phase mask is derived by replication, that is, by making an impression of the reflattened master copy.

Figure 14:
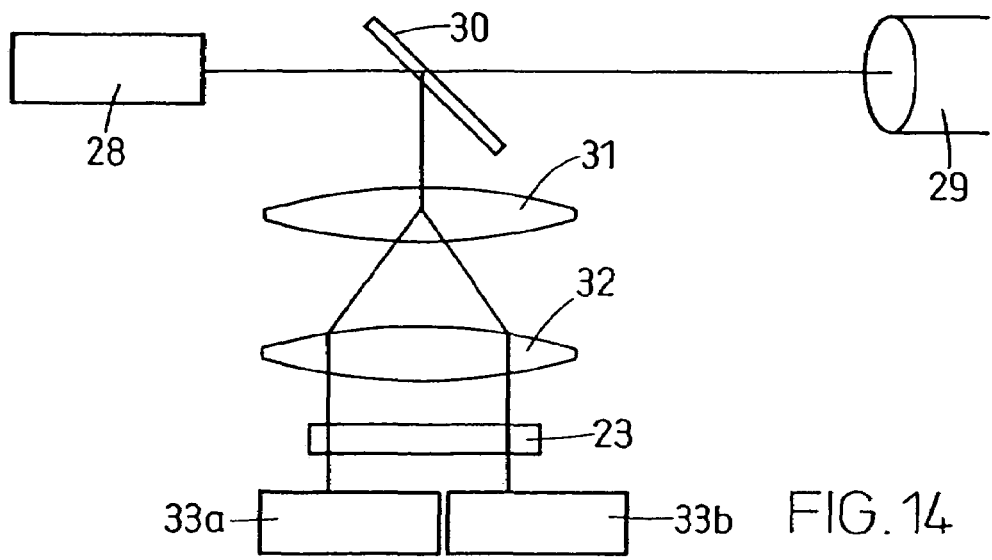

The coupler can advantageously be used in a device for monitoring and stabilising the wavelength of a laser 28 (FIG. 14) the light of which is fed into a light-conducting fibre 29, for instance a glass fibre, of a fibre network. The device comprises a semi-transmissive mirror 30 arranged in the path of the light beam coming from the laser 28, followed by a first optical system 31 to expand, and a second optical system 32 to collimate the part of the light beam deflected by the mirror 30. Following after the optical systems, the coupler 23 described above is arranged in the light beam normal to the beam direction, in such a way that the beam strikes the coupling grating 3. Mounted directly beneath the coupler 23 is a detector system with two photodetectors 33a and b which are arranged so as to be immediately adjacent one behind the other and normal to the lines in such a way that the part of the light beam transmitted by a first portion of the coupling grating 3 where the grating period is between $\square_1$ and an intermediate value $\square_i$ strikes the first photodetector 33a while the part transmitted by the remaining portion of the coupling grating 3 where the grating period is between $\square_i$ and $\square_2$ strikes the second photodetector 33b. The photodetectors 33a and b can be displaced so that Ai is adjustable.

Figure 15:
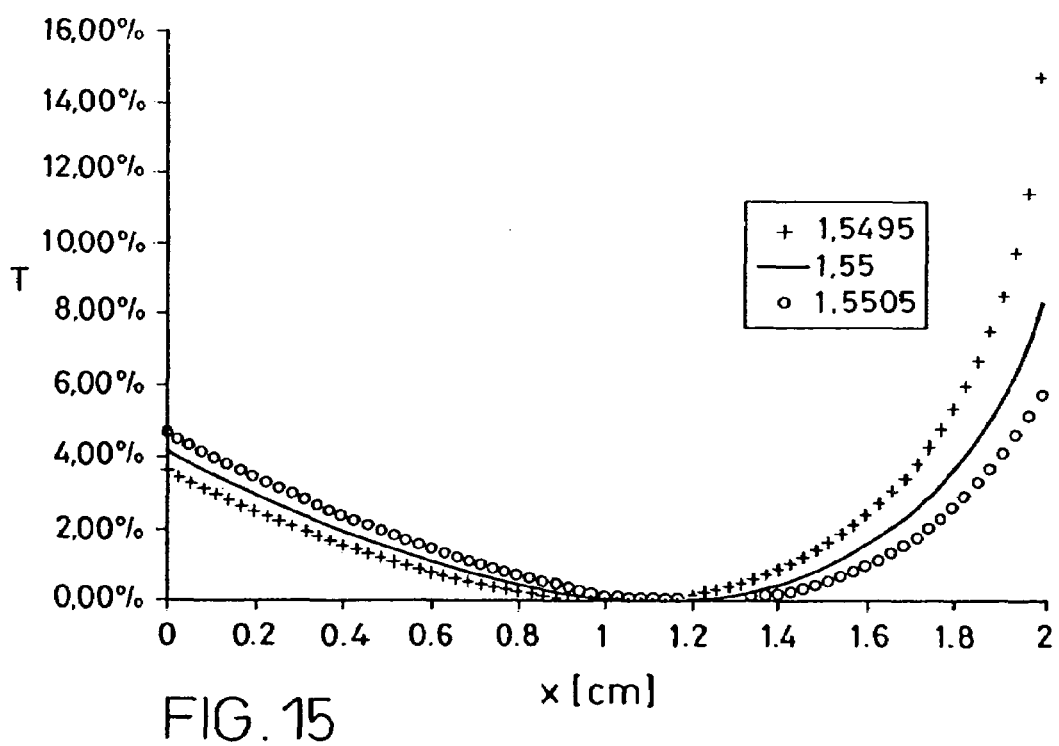
FIG. 15 shows the transmissivity of the coupler according to the third embodiment as a function of its position on the coupling grating at different wavelengths.

The transmissivity of the coupler 23 is a sensitive function of wavelength and of the grating period $\square$. Because of the position-dependent variation of the grating period $\square_{(x)}$, therefore, it exhibits a specific wavelength dependence for the incident light which depends on its position. This is shown in FIG. 15, where the transmissivity T can be gathered as a function of position on the coupling grating 3 for three very close wavelengths (1549.5 nm, 1550 nm, 1550.5 nm). The minimum of the transmissivity curve shifts to larger or smaller grating periods as the wavelengths increase or decrease, and hence to a different position on the grating. This in turn gives rise to changes in the relative intensities of the light captured by the photo-detectors 33a and 33b, which has a direct affect on the size of their output signals $I_a$ and $I_b$.

For the purposes of stabilizing a particular wavelength, one can then roughly adjust the position of the detector arrangement in accordance with the wavelength of interest, and then calculate a value $$Q=(I_a-I_b)/(I_a+I_b)$$

and reduce it to zero by shifting the detector arrangement. Any change in wavelength of the light beam coming from the laser 28 will give rise to a positive or a negative deviation of the value of Q from zero, depending on the direction of the wavelength change, and can be compensated by corresponding control of the laser 28. The intensity of the light beam is unimportant here. Only the intensity distribution of the expanded light beam which may not be homogeneous but follow a gaussian distribution, for instance, might eventually cause perturbations, but this can then be compensated by appropriate arrangement on extension of the optical systems or by calculation.

The optical elements according to the invention can be modified in many respects without departing from the basic concept of the invention. Thus, in many cases deviations from the mean value of up to 0.3_ or even up to 0.5_ over the entire element or even over a coupling grating can be admitted. For the evanescent field sensor plates and waveguide plates, too, it will often be sufficient when the changes in coupling angle $\square$ along the grating lines are not larger than 0.1_/cm.

Many deviations or special adaptations to particular requirements are possible as well in the production process. Thus, even in the exposure step which is decisive for the process, the photoresist layer may be spaced apart from the phase mask, which facilitates the process. However, it must be arranged in the near field, that is, at a distance which as a rule is smaller than 100_m, for the diffraction pattern to the sufficiently pronounced. This distance may perhaps be between 2_m and 100_m. Instead of a mercury-vapor lamp, a laser can also be used as the light source, particularly an excimer laser or an argon laser. Apart from $Ta_2O_5$, other substances can be used as materials for the layer, particularly $Nb_2O_5$, $TiO_2$, $ZrO_2$, $Al_2O_3$, $SiO_2$—$TiO_2$, $HfO_2$, $Y_2O_3$, $SiO_xN_y$, $HfO_xN_y$, $AlO_xN_y$, $TiO_xN_y$, $MgF_2$ oder $CaF_2$. Ion-enhanced evaporation or plasma-enhances gas phase deposition can be used as coating methods. Finally, several layers differing in their composition and thickness can be applied consecutively, as described in one of the embodiments portrayed.

Phase masks need not be produced directly by the two-beam interference but can be copied directly or indirectly from a master copy thus produced. They can be used several times with layers interrupted in diverse manner when diverse arrangements of coupling gratings and the like are to be generated while maintaining a constant grating period. Instead of a nontransparent layer, a suitable layer of transparent material can also be used. Thus, the grooves of the grating can be filled by a material having the refractive index of the phase mask substance.

The phase mask can be antireflection-coated. In this case, it may not be necessary to apply a reflection-reducing layer to the photoresist layer, which facilitates the production of series of grating structures on the substrates. For antireflection, a layer having a refractive index between that of the phase mask substance and that of air, and for instance consisting of $MgF_2$, is applied to the side of the phase mask facing the photoresist layer. At the same time, the grating must be adjusted in such a way that the interfering diffraction orders of the transmitted light will again have the same intensity. This adjustment can occur by changing the groove-to-land ratio and the grating depth, which are readily calculated with the aid of programs known among experts.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed:

1. A transparent substrate comprising an uninterrupted diffraction grating and a covering layer which is arranged directly on top of said diffraction grating, the covering layer being interrupted in a structured way such that it covers part of the diffraction grating and thereby optically inactivates the diffraction grating in transmission in said covered part while leaving other remaining uncovered parts of the diffraction grating exposed and active in transmission.

2. The transparent substrate according to claim 1 where the interrupted layer consists of a chromium layer.

3. The transparent substrate according to claim 1 where the interrupted layer consists of material of substantially the same index of refraction as the substrate.

4. The transparent substrate according to claim 1 where the uninterrupted diffraction grating covers a surface area of at least 10 $cm^2$.

5. A transparent substrate comprising an uninterrupted diffraction grating and a covering layer which is arranged directly on top of said diffraction grating, the covering layer being interrupted in a structured way such that it covers part of the diffraction grating and thereby optically inactivates the diffraction grating in transmission in said covered part while leaving other remaining uncovered parts of the diffraction grating exposed and active in transmission where the diffraction grating provides a pronounced diffraction pattern when exposed with a wavelength at an angle which corresponds to the Littrow angle, the diffraction pattern being limited to the vicinity below the parts of the diffraction grating which are not inactivated.

6. The transparent substrate according to claim 5 where the interrupted layer consists of a chromium layer.

7. The transparent substrate according to claim 5 where the interrupted layer consists of material of substantially the same index of refraction as the substrate.

8. The transparent substrate according to claim 5 where the uninterrupted diffraction grating covers a surface area of at least 10 cm².

9. An optical element comprising a transparent substrate according to claim 1.

10. An optical element comprising a transparent substrate according to claim 5.

11. A phasemask comprising a transparent substrate according to claim 1.

12. A phasemask comprising a transparent substrate according to claim 5.

* * * * *